United States Patent
Jang

(10) Patent No.: US 12,159,408 B2
(45) Date of Patent: Dec. 3, 2024

(54) DENTAL IMAGING MIXED REALITY SYSTEM

(71) Applicant: Andrew Timothy Jang, San Mateo, CA (US)

(72) Inventor: Andrew Timothy Jang, San Mateo, CA (US)

(73) Assignee: Andrew Jang, San Mateo, CA (US)

( * ) Notice: Subject to any disclaimer, the term of this patent is extended or adjusted under 35 U.S.C. 154(b) by 632 days.

(21) Appl. No.: 17/310,308

(22) PCT Filed: Jan. 31, 2020

(86) PCT No.: PCT/US2020/016195
§ 371 (c)(1),
(2) Date: Jul. 27, 2021

(87) PCT Pub. No.: WO2020/160461
PCT Pub. Date: Aug. 6, 2020

(65) Prior Publication Data
US 2022/0051406 A1 Feb. 17, 2022

Related U.S. Application Data

(60) Provisional application No. 62/799,938, filed on Feb. 1, 2019.

(51) Int. Cl.
G06T 7/00 (2017.01)
G06T 7/30 (2017.01)
(Continued)

(52) U.S. Cl.
CPC ............. *G06T 7/0014* (2013.01); *G06T 7/30* (2017.01); *G06T 15/08* (2013.01); *G06T 19/006* (2013.01);
(Continued)

(58) Field of Classification Search
CPC ......... G06T 7/0014; G06T 7/30; G06T 15/08; G06T 19/006; G06T 2207/10064;
(Continued)

(56) References Cited

U.S. PATENT DOCUMENTS 6,266,453 B1 7/2001 Hibbard et al.
7,929,151 B2 * 4/2011 Liang .................. A61B 1/0625
382/128

(Continued)

FOREIGN PATENT DOCUMENTS

WO WO-2020160461 A1 8/2020

OTHER PUBLICATIONS

"International Application Serial No. PCT/US2020/016195, International Preliminary Report on Patentability mailed Dec. 21, 2020", 5 pgs.

(Continued)

*Primary Examiner* — Lewis G West
(74) *Attorney, Agent, or Firm* — SCHWEGMAN LUNDBERG & WOESSNER, P.A.

(57) ABSTRACT

An imaging system is described. The imaging system accesses first imaging data of a specimen using a first sensor device. The first imaging data comprising volumetric data. The imaging system accesses second imaging data of the specimen using a second sensor device. The second imaging data comprising surface data. The imaging system registers a common anatomical region of the specimen in the first imaging data and the second imaging data and generates a composite image based on the registered common anatomical region. The composite image indicates the volumetric data and the surface data of the specimen.

18 Claims, 22 Drawing Sheets

(51) Int. Cl.
*G06T 15/08* (2011.01)
*G06T 19/00* (2011.01)

(52) U.S. Cl.
CPC ............ *G06T 2207/10024* (2013.01); *G06T 2207/10064* (2013.01); *G06T 2207/10081* (2013.01); *G06T 2207/30036* (2013.01); *G06T 2210/41* (2013.01)

(58) Field of Classification Search
CPC . G06T 2207/10081; G06T 2207/30036; G06T 2210/41; G06T 2200/04; A61B 6/51; A61B 5/0035; A61B 5/0088; A61B 5/4547; A61B 5/743; A61B 6/032; A61B 6/4085; A61B 6/5247; A61C 1/082; A61C 9/0046; A61C 19/043; A61C 2204/005
See application file for complete search history.

(56) References Cited

U.S. PATENT DOCUMENTS

| | | | | |
|---|---|---|---|---|
| 8,682,043 | B2* | 3/2014 | Cahill | A61B 6/51 382/128 |
| 9,494,418 | B2* | 11/2016 | Schmidt | A61C 9/0053 |
| 10,123,706 | B2* | 11/2018 | Elbaz | G06T 17/00 |
| 10,327,872 | B2* | 6/2019 | Verker | G02B 27/0025 |
| 11,096,586 | B1* | 8/2021 | Belthangady | A61B 5/7267 |
| 11,911,240 | B2* | 2/2024 | Sabina | A61B 6/512 |
| 2005/0283065 | A1* | 12/2005 | Babayoff | A61B 5/0088 600/407 |
| 2007/0134615 | A1* | 6/2007 | Lovely | A61B 1/063 382/128 |
| 2010/0068673 | A1* | 3/2010 | Yamada | G01N 21/474 433/29 |
| 2010/0311005 | A1* | 12/2010 | Liang | G01B 11/25 433/29 |
| 2011/0102566 | A1* | 5/2011 | Zakian | A61B 5/0086 348/66 |
| 2012/0015316 | A1* | 1/2012 | Sachdeva | A61B 1/24 382/128 |
| 2012/0170825 | A1 | 7/2012 | Vaillant | |
| 2014/0272767 | A1* | 9/2014 | Monty | A61N 5/0613 433/29 |
| 2015/0164335 | A1* | 6/2015 | Van Der Poel | A61B 5/0071 433/29 |
| 2015/0235104 | A1 | 8/2015 | Van Lierde et al. | |
| 2017/0105686 | A1 | 4/2017 | Alric et al. | |
| 2018/0005377 | A1* | 1/2018 | Alvarez | G06T 7/74 |
| 2018/0153485 | A1 | 6/2018 | Rahmes et al. | |
| 2018/0249913 | A1* | 9/2018 | Seibel | A61B 1/000094 |
| 2020/0066391 | A1* | 2/2020 | Sachdeva | G16H 20/40 |
| 2022/0148173 | A1* | 5/2022 | Minchenkov | G06N 3/044 |

OTHER PUBLICATIONS

"International Application Serial No. PCT/US2020/016195, International Search Report mailed May 4, 2020", 2 pgs.
"International Application Serial No. PCT/US2020/016195, Written Opinion mailed May 4, 2020", 8 pgs.

* cited by examiner

DENTAL IMAGING MIXED REALITY SYSTEM

CROSS-REFERENCE TO RELATED APPLICATIONS

[1] The present application is a U.S. National Stage Filing under 35 U.S.C. 371 from International Application No. PCT/US2020/016195, filed on Jan. 31, 2020, and published as WO 2020/160461 on Aug. 6, 2020, which application claims priority to U.S. Provisional Patent Application Ser. No. 62/799,938, filed Feb. 1, 2019, which is are hereby incorporated by reference in its-their entirety.

BACKGROUND

The subject matter disclosed herein generally relates to the processing of data. Specifically, the present disclosure addresses systems and methods for processing dental images and providing augmented information on a composite three-dimensional model based on the dental images.

Current techniques for assessing periodontal health involves a dentist manually measuring gum disease of a patient at different points with a dental instrument. This manual procedure does not allow the dentist or the patient to easily visualize a current state of gum disease of the patient. Furthermore, it is difficult for the dentist to examine a region of interest (e.g., dental caries) in the mouth of the patient and especially, the position of an instrument (inside the mouth of the patient) relative to the region of interest.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
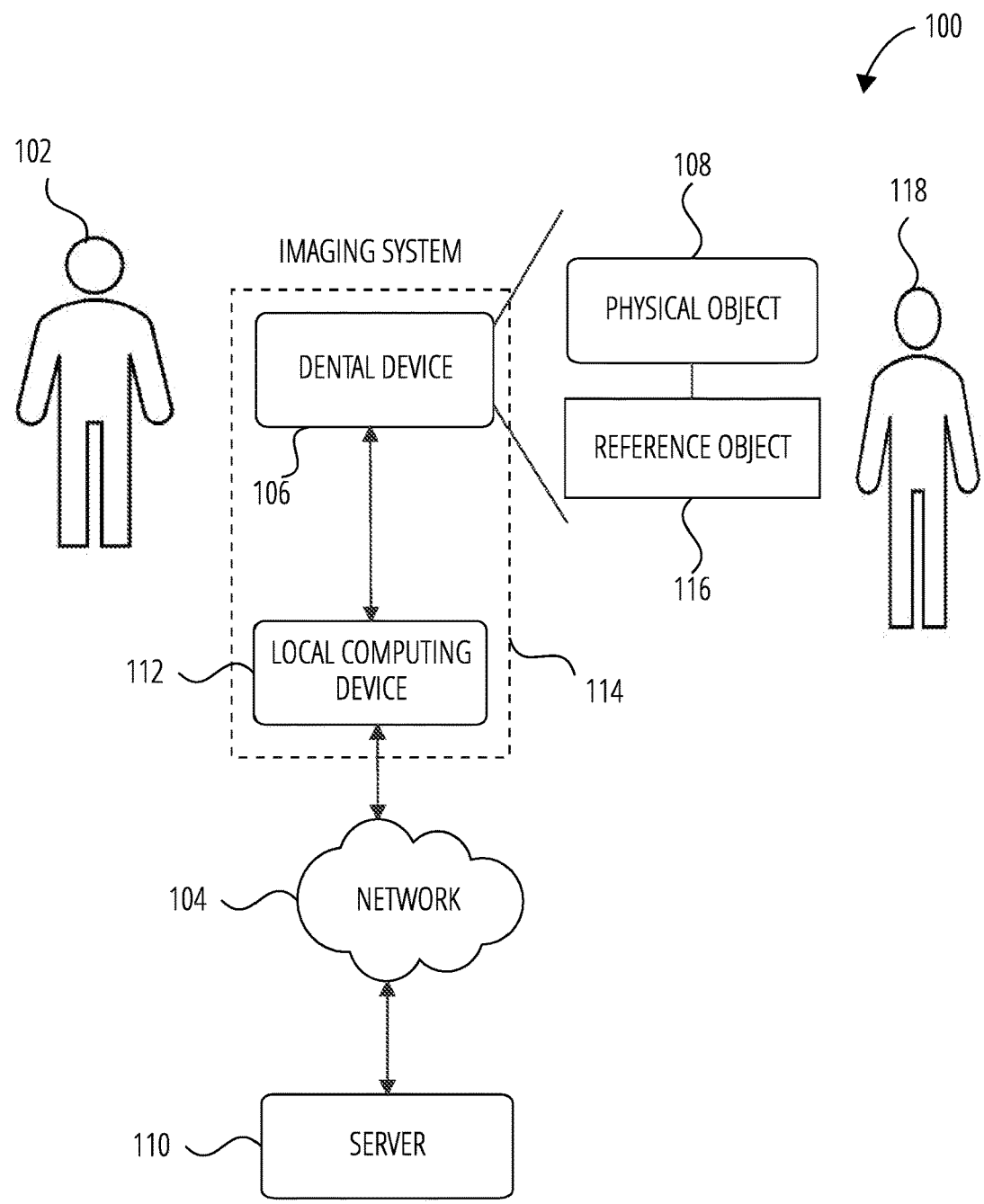
FIG. 1 illustrates a network environment for operating an imaging system in accordance with one example embodiment.

Example methods and systems are directed to a method for dental imaging with augmented information. Examples merely typify possible variations. Unless explicitly stated otherwise, components and functions are optional and may be combined or subdivided, and operations may vary in sequence or be combined or subdivided. In the following description, for purposes of explanation, numerous specific details are set forth to provide a thorough understanding of example embodiments. It will be evident to one skilled in the art, however, that the present subject matter may be practiced without these specific details.

The present application describes a method for providing diagnostic information regarding a patient's oral periodontal health. Current methods are slow, painful, and inaccurate (e.g., a dentist pokes a patient's gum line with a little thin stick and calls out arbitrary numbers). In one example embodiment, the information from two or more imaging techniques (e.g., intraoral scanner and cone beam computerized tomography) is combined and provides additional information that cannot be determined using the individual components separately.

The present application also describes a method for virtual positioning of a dental instrument in relation to a particular "region of interest" for a dental procedure. For example, a region of interest may include a location of cavities when drilling a filling (also can be used to locate tooth nerve when performing a filling), a location of bone for implant placement, and a location of target nerve for tough anesthetic injections. Currently, the dentist assesses or estimates the region of interest based on visible external landmarks in the mouth of the patient.

The present application describes a comprehensive assessment of a person's periodontal health and individualized anatomical landmarks based on multiple imaging sources and augment a clinician's clinical tools (e.g., handpiece) to virtually interact/position itself in the same digital workspace.

Example advantages of digital diagnosis include:
  imaging can be performed by auxiliary dental staff, accurate than the traditional methods of measuring gum diseases (3 point measurements on the gum) which makes it easy to miss;
  easier visualization by the doctor and patients (patient education and easier to "sell" treatment);
  quantity different markers of periodontal (e.g., gum) health instantaneously. The imaging data can be used to improve gum measurement over time (e.g., via machine learning model) and visualize health trends.

Example advantage of augmented reality for dental tools include:
  more precise than just guessing using local landmarks;
  can be used to definitively avoid problem areas (e.g., nerve chamber when drilling a tooth for a filling);
  can be used for multiple types of dental procedures (e.g., fillings, crown preps, injections)—system can be used with interchangeable parts;
  can be integrated into normal dental workflow (uses tools that dentists are comfortable with).

In one example embodiment, the present application describes a method comprising: accessing first imaging data of a specimen using a first sensor device, the first imaging data comprising volumetric data; accessing second imaging data of the specimen using a second sensor device, the second imaging data comprising surface data; and generating a composite image based on the first and second imaging data, the composite image indicating the volumetric data and the surface data of the specimen.

In another example embodiment, a non-transitory machine-readable storage device may store a set of instructions that, when executed by at least one processor, causes the at least one processor to perform the method operations discussed within the present disclosure.

FIG. 1 is a network diagram illustrating a network environment 100 suitable for operating a dental device 106, according to some example embodiments. The network environment 100 includes an imaging system 114 and a server 110, communicatively coupled to each other via a network 104. The imaging system 114 and the server 110 may each be implemented in a computer system, in whole or in part, as described below with respect to FIG. 22.

The server 110 may be part of a network-based system. For example, the network-based system may be or include a cloud-based server system that provides additional information, such as three-dimensional models of specimens, to the imaging system 114.

FIG. 1 illustrates a user 102 using the imaging system 114. The user 102 may be a human user (e.g., a human being), a machine user (e.g., a computer configured by a software program to interact with the dental device 106), or any suitable combination thereof (e.g., a human assisted by a machine or a machine supervised by a human). The user 102 is not part of the network environment 100, but is associated with the imaging system 114 and may be a user 102 of the imaging system 114.

The imaging system 114 includes a dental device 106 and a local computing device 112. The dental device 106 may include a dental instrument such as a dental handpiece, scalpel, syringe.

The local computing device 112 may be a computing device with a display such as a smartphone, a tablet computer, or a laptop computer. The user 102 may be a user of an application in the local computing device 112. The application may include an imaging application configured to detect a region of interest (e.g., gum disease) at the physical object 108 and provide a visualization of the region of interest to the user 102. In one example embodiment, the physical object 108 includes a mouth/gum/teeth of a patient 118. The reference object 116 is temporarily coupled to the mouth of the patient 118. For example, the reference object 116 includes a custom-bite block that the patient 118 bites.

The dental device 106 is capable of tracking its relative position and orientation in space relative to the reference object 116. For example, the dental device 106 includes optical sensors (e.g., depth-enabled 3D camera, image camera), inertial sensors (e.g., gyroscope, accelerometer), wireless sensors (Bluetooth, Wi-Fi), and GPS sensor, to determine the location of the dental device 106 within a real world environment. In another example, the location, position, and orientation of the dental device 106 is determined relative to the reference object 116 (e.g., an object that is coupled and remains temporarily fixed to the teeth of a patient).

Any of the machines, databases, or devices shown in FIG. 1 may be implemented in a general-purpose computer modified (e.g., configured or programmed) by software to be a special-purpose computer to perform one or more of the functions described herein for that machine, database, or device. For example, a computer system able to implement any one or more of the methodologies described herein is discussed below with respect to FIG. 6 to FIG. 8. As used herein, a "database" is a data storage resource and may store data structured as a text file, a table, a spreadsheet, a relational database (e.g., an object-relational database), a triple store, a hierarchical data store, or any suitable combination thereof. Moreover, any two or more of the machines, databases, or devices illustrated in FIG. 1 may be combined into a single machine, and the functions described herein for any single machine, database, or device may be subdivided among multiple machines, databases, or devices.

The network 104 may be any network that enables communication between or among machines (e.g., server 110), databases, and devices (e.g., dental device 106). Accordingly, the network 104 may be a wired network, a wireless network (e.g., a mobile or cellular network), or any suitable combination thereof. The network 104 may include one or more portions that constitute a private network, a public network (e.g., the Internet), or any suitable combination thereof.

Figure 2:
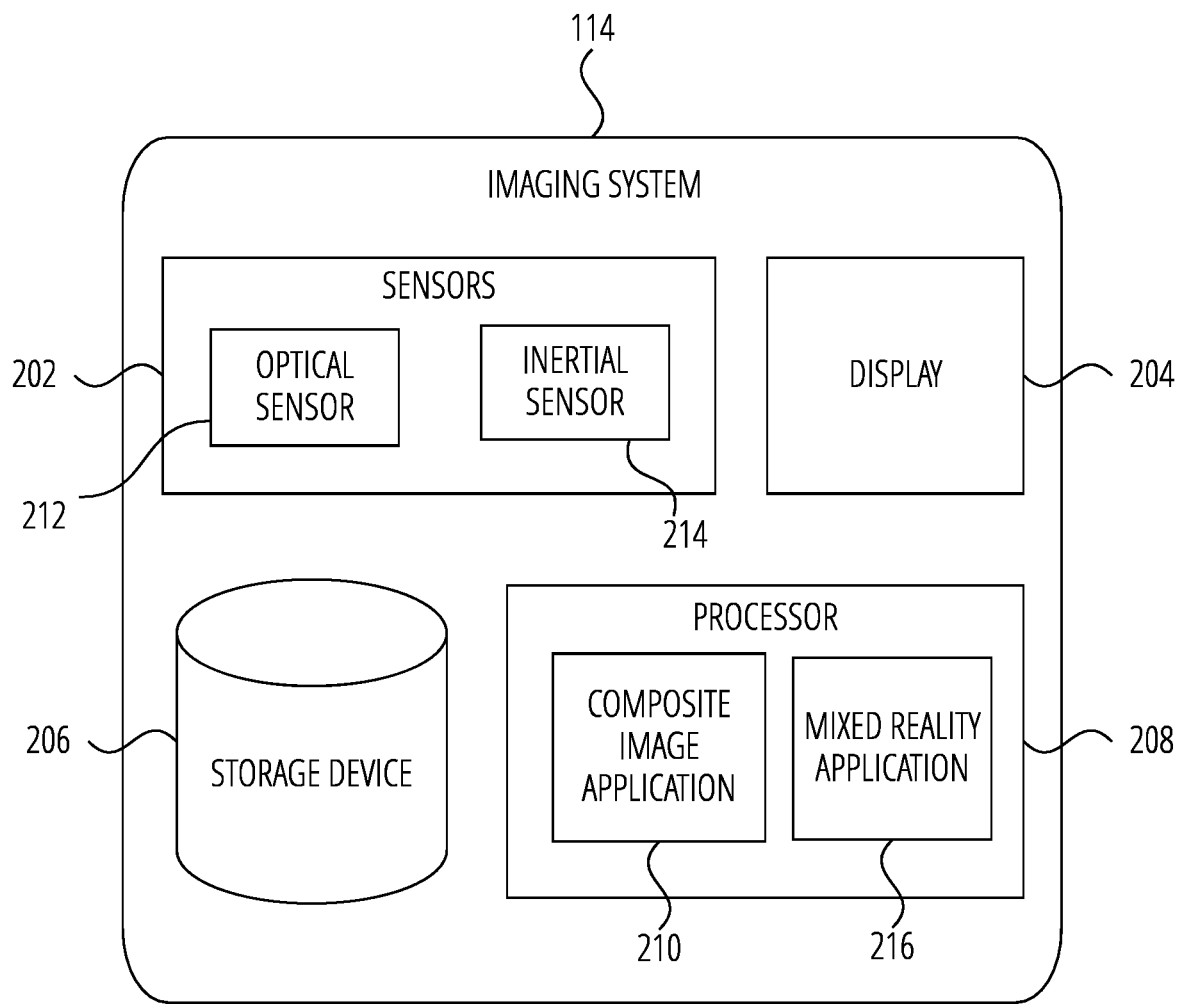
FIG. 2 illustrates an imaging system in accordance with one example embodiment.

FIG. 2 is a block diagram illustrating modules (e.g., components) of the imaging system 114, according to some example embodiments. The imaging system 114 includes sensors 202, a display 204, a storage device 206, a processor 208, a composite image application 210, a mixed reality application 216, an optical sensor 212, and an inertial sensor 214.

The processor 208 includes the composite image application 210 and the mixed reality application 216. The composite image application 210 generates a composite image based on different image sources (e.g., intraoral and CBCT). The composite image includes a visual indication of the region of the interest (e.g., gingival surface). The mixed reality application 216 generates augmented information based on the location of the dental device 106 and the three-dimensional model of the teeth and gum of the patient.

The mixed reality application 216 merges information from the real and virtual world to produce new environments and visualizations, where physical and digital objects co-exist and interact in real-time. Mixed reality is a hybrid of augmented reality (AR) and virtual reality (VR). In one example, the mixed reality application 216 includes a combination of AR and VR aspects.

In one example, the mixed reality application 216 includes an AR application that allows the user 102 to experience information, such as in the form of a three-dimensional (or two-dimensional) virtual object overlaid on an image of the physical object 108 captured by a camera of the imaging system 114. The physical object 108 may include a visual reference that the AR application can identify. A visualization of the additional information, such as the three-dimensional virtual object overlaid or engaged with an image of the physical object 108, is generated in a display of the imaging system 114. The three-dimensional virtual object may be selected based on the recognized visual reference (e.g., reference object 116) or captured image of the physical object 108. A rendering of the visualization of the three-dimensional virtual object may be based on a position of the display relative to the reference object 116. Other augmented reality applications allow a user to experience visualization of the additional information overlaid on top of a view or an image of any object in the real physical world. The virtual object may include a three-dimensional virtual object, a two-dimensional virtual object. An image of the virtual object may be rendered at the imaging system 114.

In one example, a system and method for creating virtual content using a head-mounted device is described. The head-mounted device can be used to create virtual content without using a client device (e.g., laptop or desktop). The wearer of the head-mounted device determines virtual content to be associated with the physical object 108. The head-mounted device then associates the virtual user interface with identifiers of the physical object 108 and tracking data related to the physical object 108. The virtual user interface is displayed in relation to the image of the physical object 108.

In another example, the mixed reality application 216 displays the augmented information in a display screen of the local computing device 112.

In one example embodiment, the imaging system 114 may communicate over the network 104 with the server 110 to retrieve a portion of a database of visual references (e.g., images from different specimens).

Any one or more of the modules described herein may be implemented using hardware (e.g., a processor of a machine) or a combination of hardware and software. For example, any module described herein may configure a processor to perform the operations described herein for that module. Moreover, any two or more of these modules may be combined into a single module, and the functions described herein for a single module may be subdivided among multiple modules. Furthermore, according to various example embodiments, modules described herein as being implemented within a single machine, database, or device may be distributed across multiple machines, databases, or devices.

Figure 3:
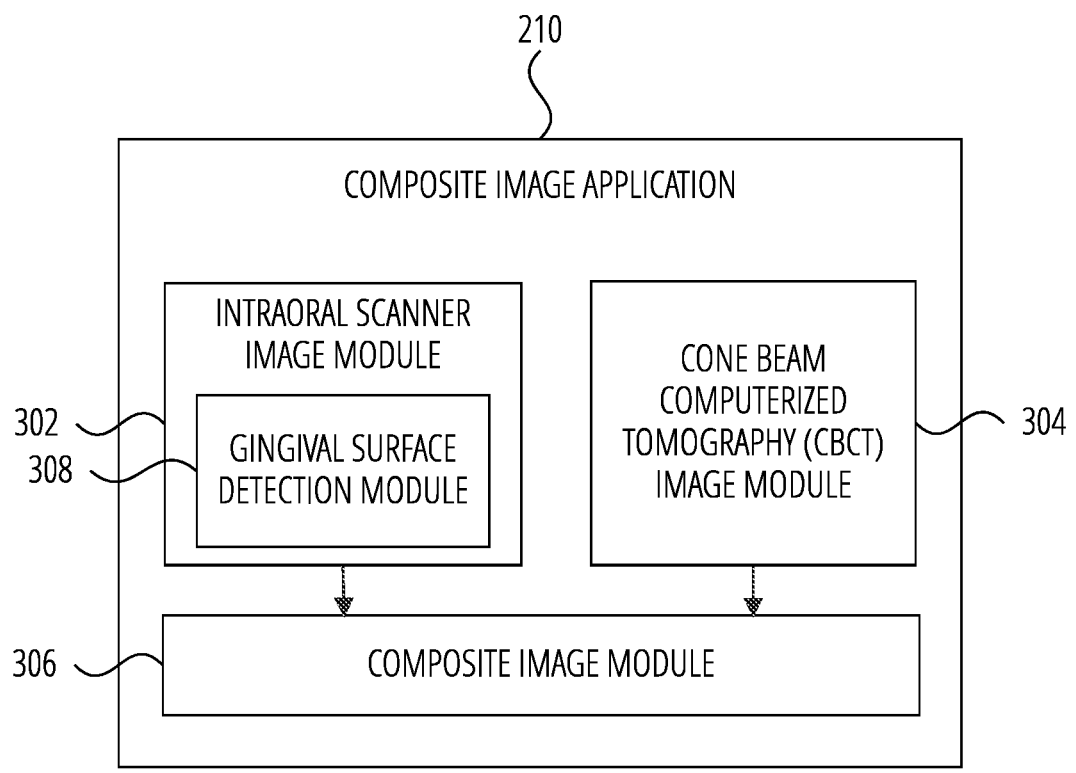
FIG. 3 illustrates a composite image application in accordance with one example embodiment.

FIG. 3 illustrates a composite image application in accordance with one example embodiment. The composite image application 210 generates a composite image based on different image sources (e.g., intraoral and CBCT). The composite image includes a visual indication of the region of the interest (e.g., gingival surface). In one example, the composite image application 210 comprises an intraoral scanner image module 302, a cone beam computerized tomography (CBCT) image module 304, a composite image module 306, and a gingival surface detection module 308.

The intraoral scanner image module 302 communicates with an intraoral scanner and accesses first image data of the patient 118 from the intraoral scanner. Examples of intraoral scanner include, but are not limited to, light projection and capture, laser confocal, AWS (Active Wavefront Sampling), and stereo-photogrammetry.

The intraoral scanner image module 302 includes a gingival surface detection module 308 that detects gingival surface based on the first image data. For example, the gingival surface detection module 308 determines depth of tissue based on the image data and compares the depth of tissue to a predefined lookup table of gingival depth.

The cone beam computerized tomography (CBCT) image module 304 communicates with a cone beam computerized tomography (CBCT) and accesses second image data of the patient 118 from the CBCT.

The composite image module 306 generates a composite image (of the patient 118's teeth/gum) based on the first image data from the intraoral scanner image module 302 and the second image data from the cone beam computerized tomography (CBCT) image module 304. In one example, the composite image module 306 uses image segmentation, image registration/alignment of images to generate the composite image. For example, the composite image module 306 identifies a common region of the specimen in the first imaging data and the second imaging data and aligns the first imaging data with the second imaging data based on the identified common region. The composite image module 306 registering the composite image when the common regions of the specimen are aligned in the imaging data.

Figure 4:
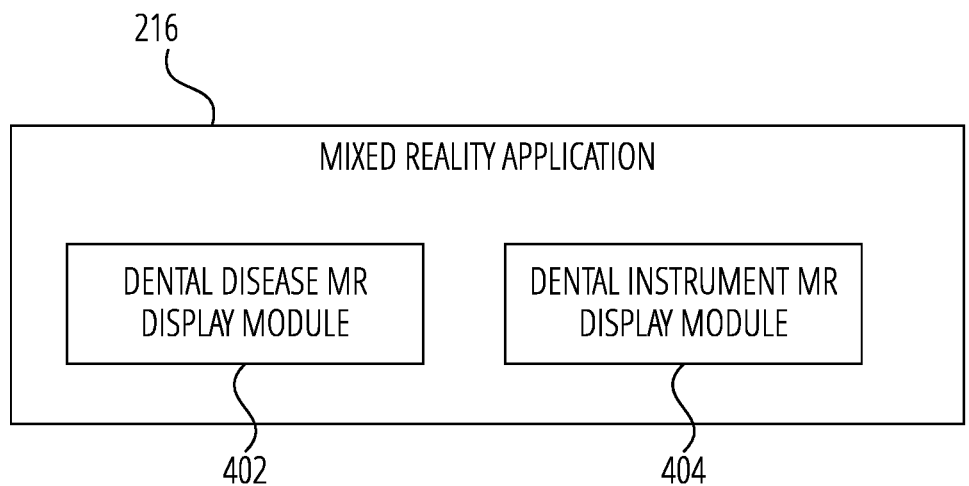
FIG. 4 illustrates a mixed reality (MR) application in accordance with one example embodiment.

FIG. 4 illustrates an augmented reality (AR) application in accordance with one example embodiment. The mixed reality application 216 generates augmented information based on the location of the dental device 106 and the three-dimensional model of the teeth and gum of the patient 118.

In one example, mixed reality application 216 comprises dental disease MR display module 402 and dental instrument MR display module 404. The dental disease MR display module 402 indicates a region of interest in a display of the 3D model. For example, the dental disease MR display module 402 indicates a tooth decay area in a display of the 3D model, a suggested shape for a root canal in a display of the 3D model, regions of the tooth for removal for a crown procedure in a display of the 3D model, or a bone region of a projected injection site in a display of the 3D model.

The dental instrument MR display module 404 displays a virtual representation of the dental device 106 relative to the 3D model of the mouth of the patient 118 (e.g., teeth and gum of the patient 118). In one example, the location of the dental device 106 is determined relative to the reference object 116 based on the sensors in dental device 106 and reference object 116.

In other example embodiment, the mixed reality application 216 can be used for medical and surgical procedures to display in real-time an image of a surgical instrument operated by a medical professional in relation to digital information that indicate an area of interest on a real-time image of a body part of the patient.

Figure 5:
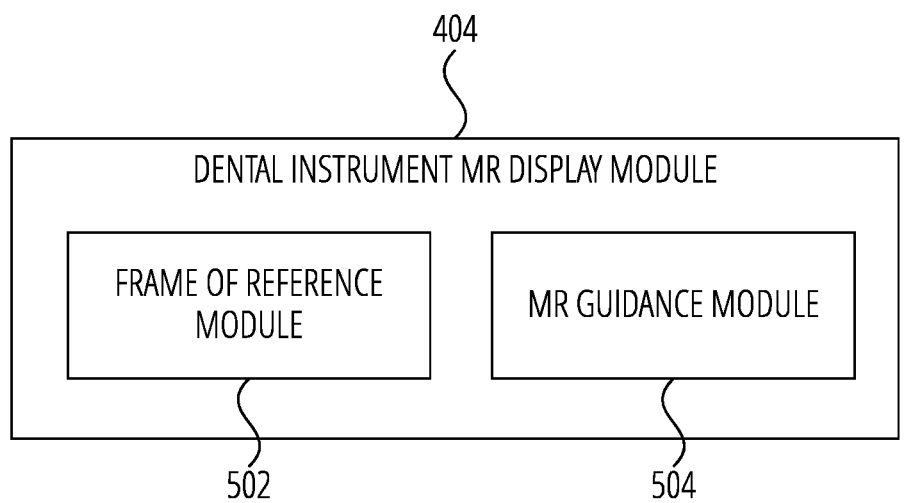
FIG. 5 illustrates a dental disease MR display module in accordance with one example embodiment.

FIG. 5 illustrates a dental disease AR display module in accordance with one example embodiment. The dental instrument MR display module 404 includes a frame of reference module 502, and an MR guidance module 504. The frame of reference module 502 determines a location of the sensors in the dental device 106 relative to the sensors in the reference object 116. In one example, the sensors include a combination of a gyroscope, an accelerometer, inertial sensor 214, wireless communication device (e.g., Bluetooth, WiFi), or any other sensor that detects a position, location, orientation of the sensors in the dental device 106 relative to the sensors in the reference object 116. In another example, the sensors in the dental device 106 communicate with the sensors in the reference object 116. In yet another example, the sensors in the dental device 106 and the sensors in the reference object 116 both communicate with the frame of reference module 502. In yet another example, the frame of reference module 502 uses the optical sensor 212 to detect a position, location, orientation of the sensors in the dental device 106. For example, the frame of reference module 502 detects a first unique visual marker of the dental instrument and a second unique visual marker of the reference object 116. The frame of reference module 502 can thus determine a relative distance, position, and orientation of the dental device 106 relative to the reference object 116.

It is noted that the sensors of the dental device 106 are positioned at a predefined location on the dental device 106. For example, the distance between a tip of the dental instrument and the sensors in the dental device 106 are predefined. In one example, the sensors may be coupled to any portion of the dental device 106. A lookup table that defines the relative distances may be updated based on the measured distances between the sensors and other portions of the dental device 106.

In one example, the reference object 116 is at a predetermined location relative to the teeth of the patient. Sensors in the reference object 116 are located at a predefined distance related to the reference object 116. For example, the distance between an end of the reference object 116 and the sensors in the reference object 116 are predefined. In one example, the sensors may be coupled to any portion of the reference object 116. A lookup table that defines the relative distances may be updated based on the measured distances between the sensors and other portions of the reference object 116. In another example embodiment, the reference object 116 is custom-printed or custom-shaped based on the teeth of the patient.

The MR guidance module 504 determines a relative position, location, orientation of the dental device 106 relative to the reference object 116. In another example, the MR guidance module 504 determines the relative distance between the dental device 106 and the reference object 116.

The MR guidance module 504 accesses a 3D model (or a composite image) of the teeth/gum of the patient. The MR guidance module 504 initializes and calibrates the location of the reference object 116 relative to the teeth of the patient based on the predefined distance/location between the reference object 116 relative to the teeth of the patient, and the predefined distance/location between the sensors of the reference object 116 relative to the reference object 116.

The MR guidance module 504 determines a location of the dental device 106 relative to the reference object 116 based on the detected position, location, orientation of the dental device 106 relative to the reference object 116.

The MR guidance module 504 causes a display of a virtual dental instrument (or any other type of visual indicator) relative to the 3D model (or composite image) of the teeth/gum of the patient 118 based on the position, location, orientation and distance of the sensors in the dental device 106 relative to the reference object 116. As such, the MR guidance module 504 provides real-time feedback (of the location of the dental device 106) to the user 102 (e.g., dentist) of the imaging system 114.

In another example, the MR guidance module 504 causes display of a region of interest in the 3D model or composite image based on the dental disease MR display module 402. For example, the MR guidance module 504 displays the location of the dental device 106 relative to a highlighted region of interest in the 3D model or composite image. In another example, the MR guidance module 504 provides virtual display indicators in display 204 to guide the user 102 on how to perform a procedure (e.g., where to position and operate the dental device 106 on the patient 118).

Figure 6:
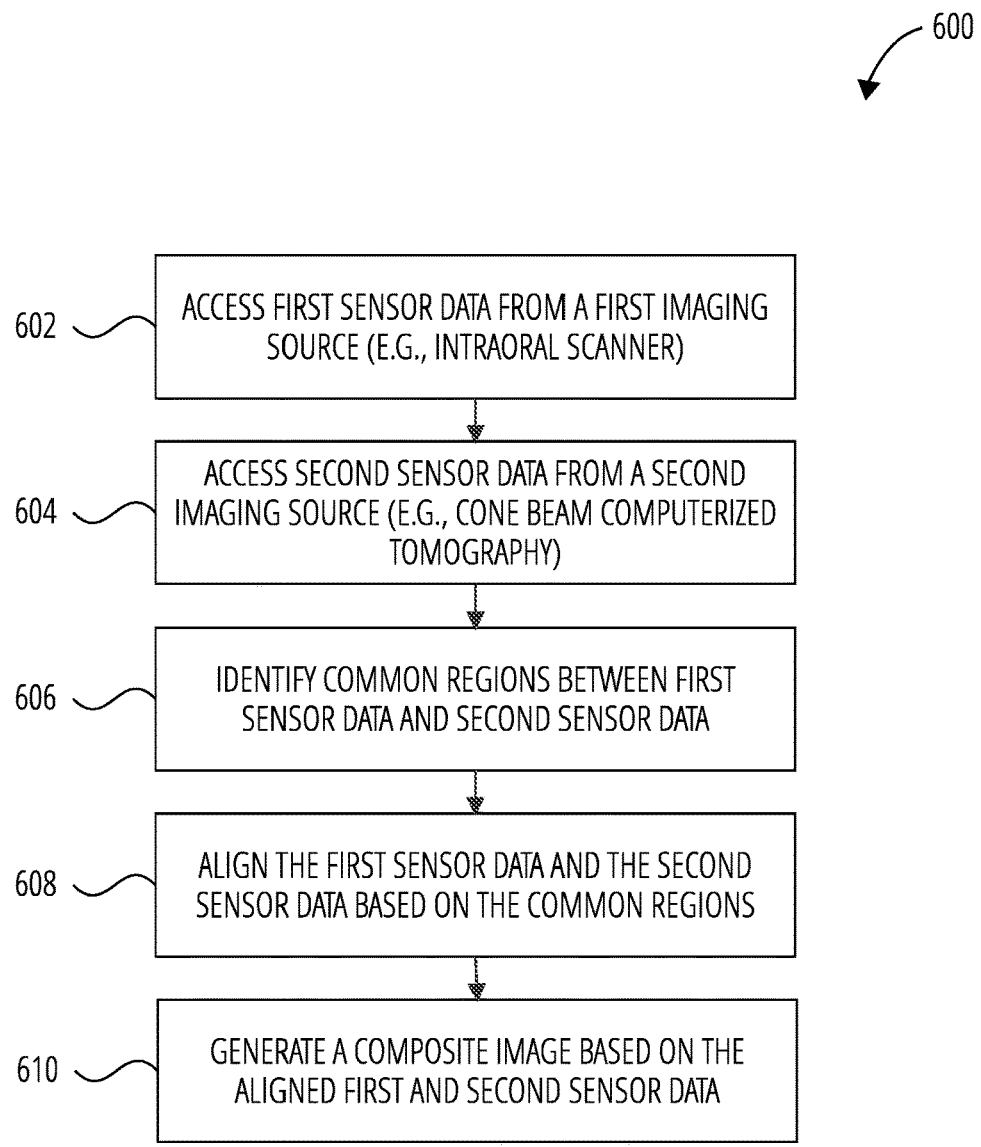
FIG. 6 illustrates a method for generating a composite image in accordance with one example embodiment.

FIG. 6 illustrates a method 600 for generating a composite image in accordance with one example embodiment. At block 602, the composite image application 210 accesses first sensor data from a first imaging source (e.g., intraoral scanner). At block 604, the composite image application 210 accesses second sensor data from a second imaging source (e.g., cone beam computerized tomography). At block 606, the composite image application 210 identifies common regions between the first sensor data and second sensor data (e.g., same parts of a tooth). At block 608, the composite image application 210 aligns the first sensor data and the second sensor data based on the common regions. At block 610, the composite image application 210 generates a composite image based on the aligned first and second sensor data.

Figure 7:
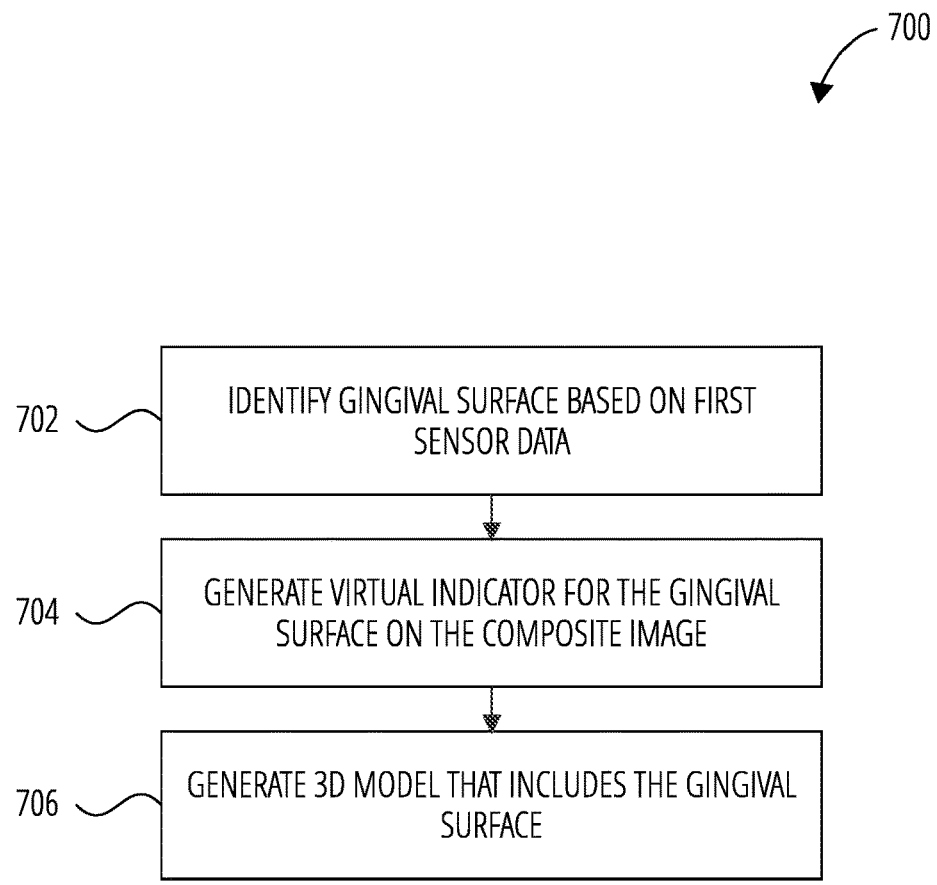
FIG. 7 illustrates a method for generating a 3D model in accordance with one example embodiment.

FIG. 7 illustrates a method 700 for generating a 3D model in accordance with one example embodiment. At block 702, the composite image application 210 identifies gingival surface based on first sensor data. At block 704, the composite image application 210 generates virtual indicator for the gingival surface on the composite image. At block 706, the composite image application 210 generates a 3D model that includes the gingival surface.

Figure 8:
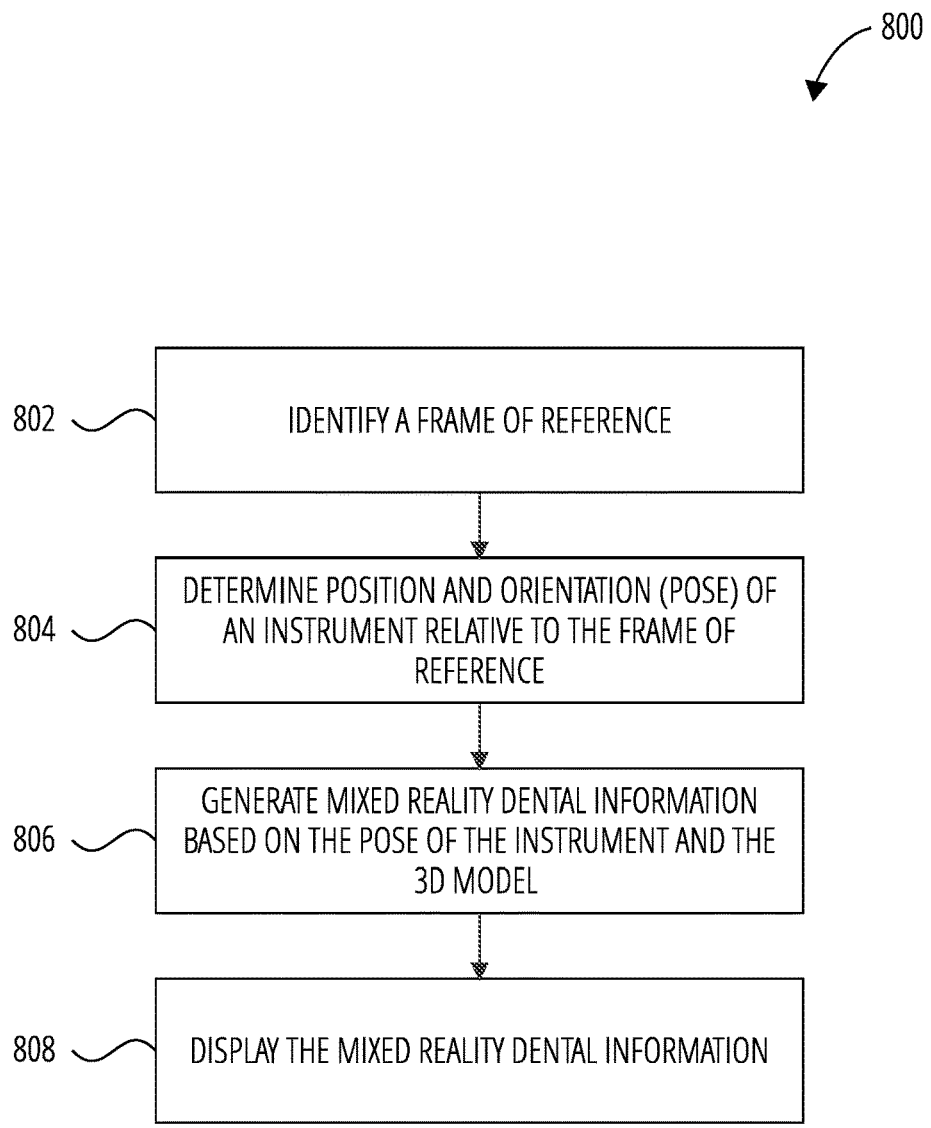
FIG. 8 illustrates a method for generating MR information in accordance with one example embodiment.
Figure 9:
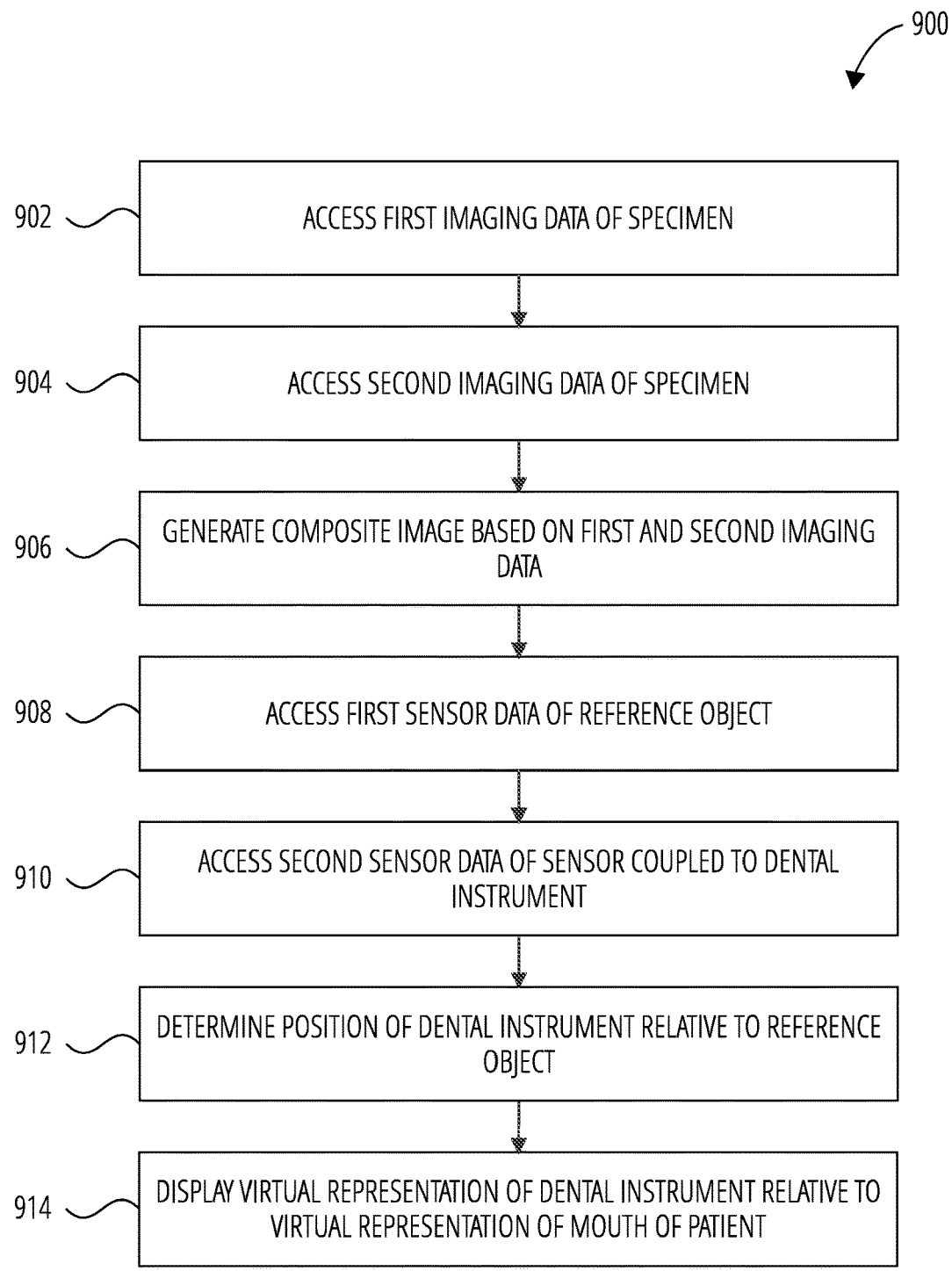
FIG. 9 illustrates a routine 900 in accordance with one embodiment.

FIG. 8 illustrates a method 800 for generating AR information in accordance with one example embodiment. At block 802, the mixed reality application 216 identifies a frame of reference by detecting the location of the reference object 116. At block 804, the mixed reality application 216 determines a position and orientation (pose) of an instrument relative to the reference object 116. At block 806, the mixed reality application 216 generates mixed reality dental information (e.g., digital information that is superimposed on a live view or a real-time display of the teeth of the patient 118). The mixed reality dental information is based on the pose (e.g., location, orientation, position) of the dental device 106 relative to the 3D model. At block 808, the mixed reality application 216 displays the mixed reality dental information in the display 204.

In block 902, routine 900 accesses first imaging data of a specimen using a first sensor device, the first imaging data comprising volumetric data. In block 904, routine 900 accesses second imaging data of the specimen using a second sensor device, the second imaging data comprising surface data. In block 906, routine 900 generates a composite image based on the first and second imaging data, the composite image indicating the volumetric data and the surface data of the specimen. In block 908, routine 900 accesses first sensor data of a reference object resting in a mouth of a patient, the reference object being at a predefined position relative to the mouth of the patient. In block 910, routine 900 accesses second sensor data of a sensor coupled to a dental instrument. In block 912, routine 900 determines a position of the dental instrument relative to the reference object based on the first and second sensor data. In block 914, routine 900 displays a virtual representation of the dental instrument relative to a virtual representation of the mouth of the patient based on the position of the dental instrument relative to the reference object.

Figure 10:
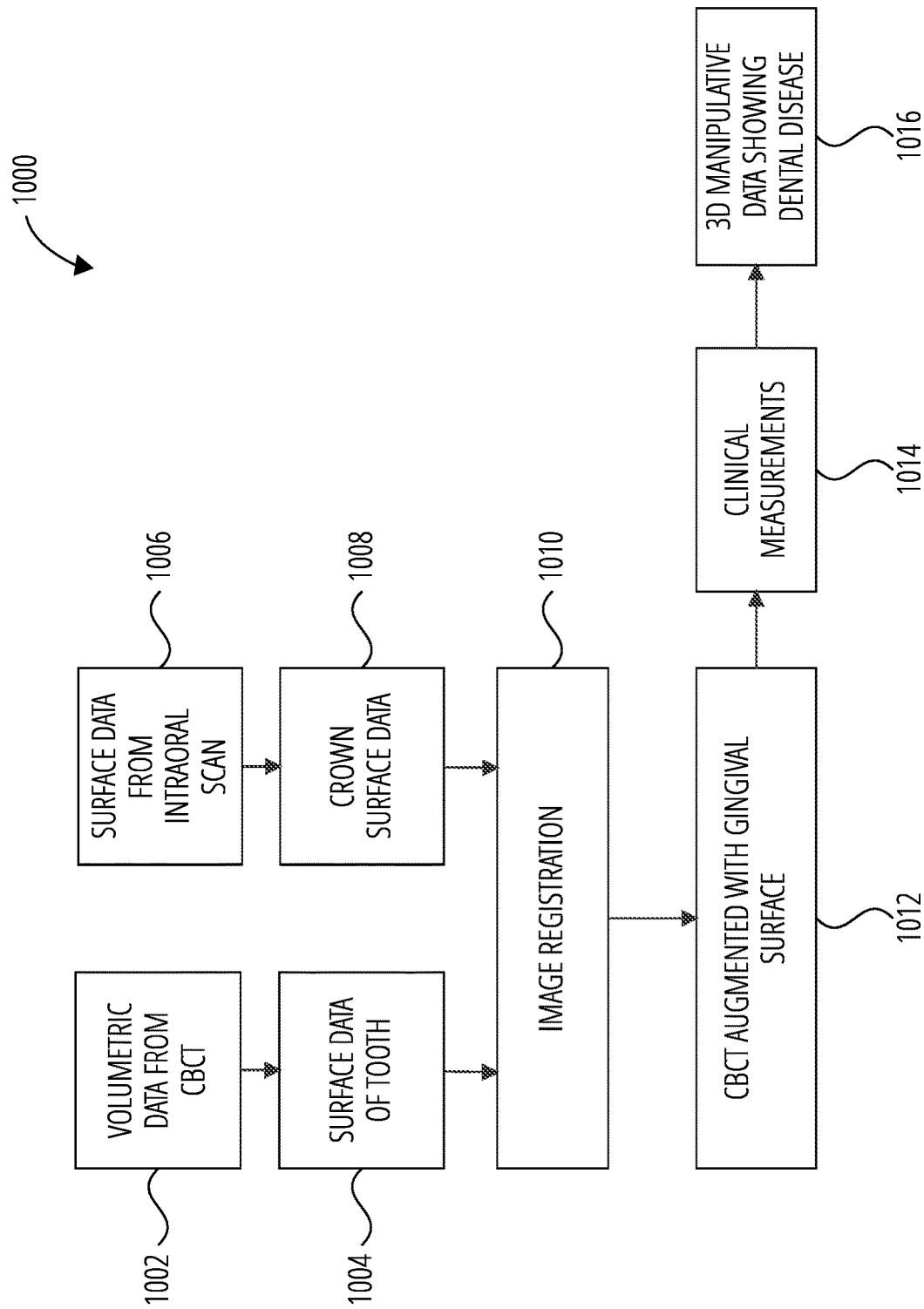
FIG. 10 illustrates an example operation of the composite image application in accordance with one example embodiment.

FIG. 10 illustrates an example process 1000 of the composite image application 210 in accordance with one example embodiment. The volumetric data from CBCT 1002 provide surface data of tooth 1004. The surface data from intraoral scan 1006 is used to identify crown surface data 1008. At image registration 1010, both the surface data of tooth 1004 and crown surface data 1008 are registered to generate a composite image. The composite image indicates CBCT augmented with gingival surface 1012 that can be used for clinical measurements 1014. Examples of clinical measurements 1014 include pocket depth, tissue biotype, and areas of inflammation. Data from the clinical measurements 1014 can be used to generate 3D manipulative data showing dental disease 1016.

Figure 11:
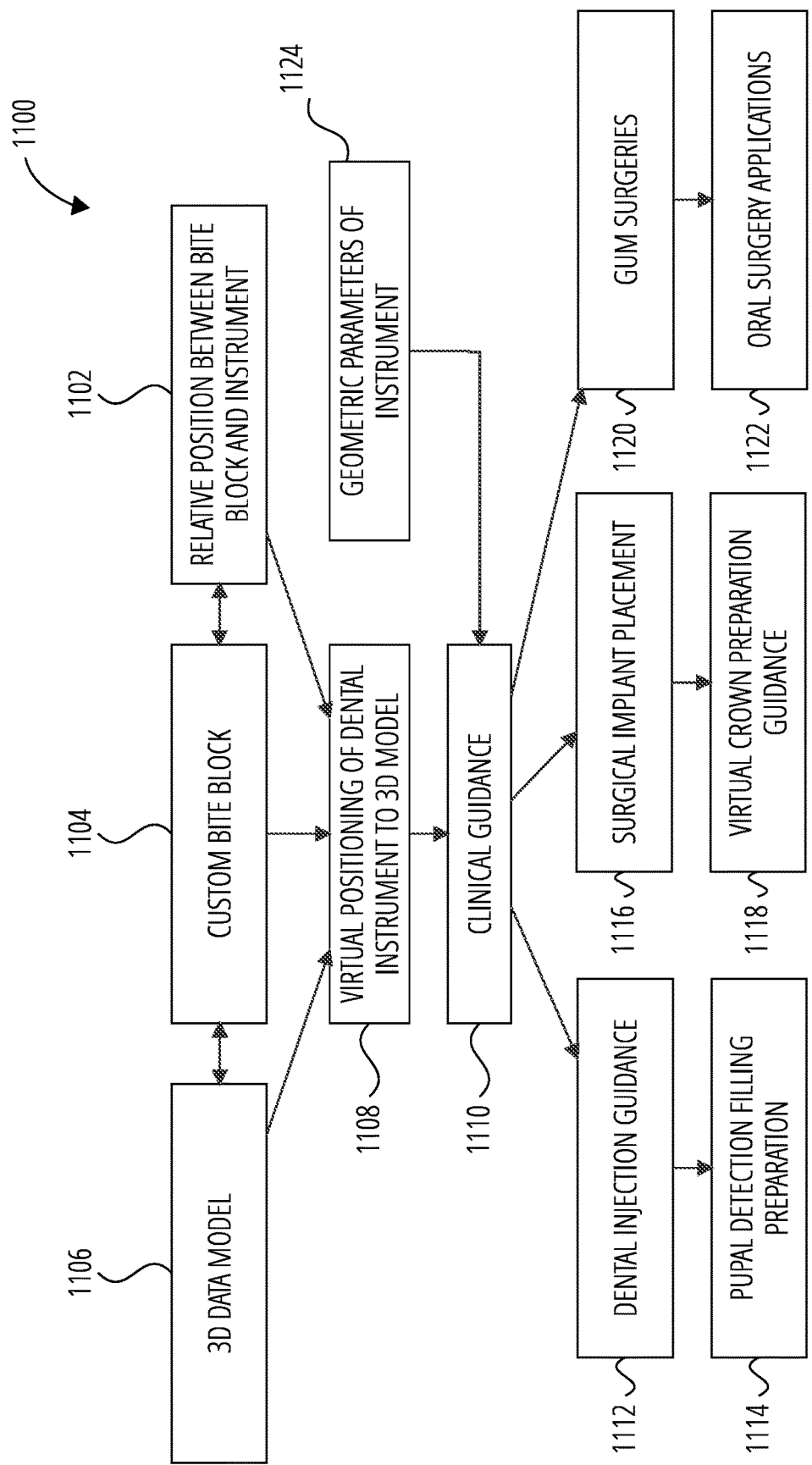
FIG. 11 illustrates an example operation of the dental instrument MR display module in accordance with one example embodiment.

FIG. 11 illustrates an example process 1100 of the dental instrument MR display module 404 in accordance with one example embodiment. In block 1108, the virtual positioning of the dental device 106 relative to the patient 118 is based on a reference object 116 (e.g., 3D printed custom bite block with sensors) positioned inside the mouth of the patient 118 at block 1104 and the relative position (e.g., 6 axis relative position) between the reference object 116 and the dental device 106 at block 1102. The virtual positioning of the dental device 106 relative to custom bite block inside the patient 118 is also based on the 3D data model showing dental disease and anatomical features at block 1106.

The geometric parameters (e.g., bur dimension, needle length) of the dental device 106 at block 1124 are used along with the virtual positioning of the dental device 106 for clinical guidance at block 1110. Examples of clinical guidance include dental injection guidance at block 1112, surgical implant placement at block 1116, and gum surgeries at block 1120, pulpal detection for filling preparation at block 1114, virtual crown preparation guidance (e.g., occlusal reduction) at block 1118, and oral surgery applications (e.g., biopsy) at block 1122.

Figure 12:
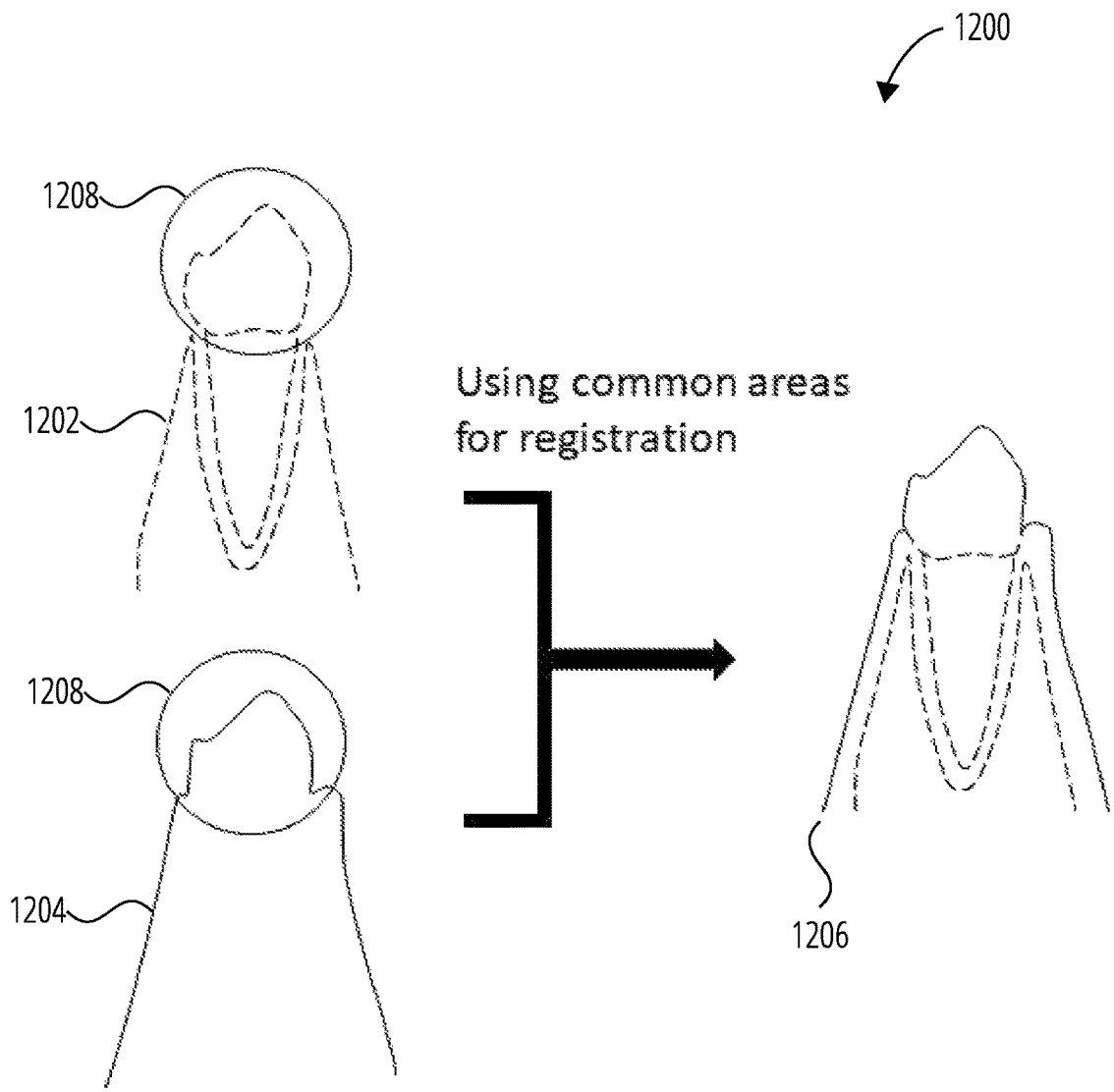
FIG. 12 illustrates an example of combining a first and second dental imaging data to generate a composite image in accordance with one example embodiment.

FIG. 12 illustrates an example 1200 of combining a first and second dental imaging data to generate a composite image in accordance with one example embodiment. A common region 1208 that is common to both the soft tissue image 1202 and the tooth surface image 1204 is identified. The imaging system 114 uses the common region 1208 for registration and combines both the soft tissue image 1202 and the tooth surface image 1204 into a composite image 1206.

Figure 13:
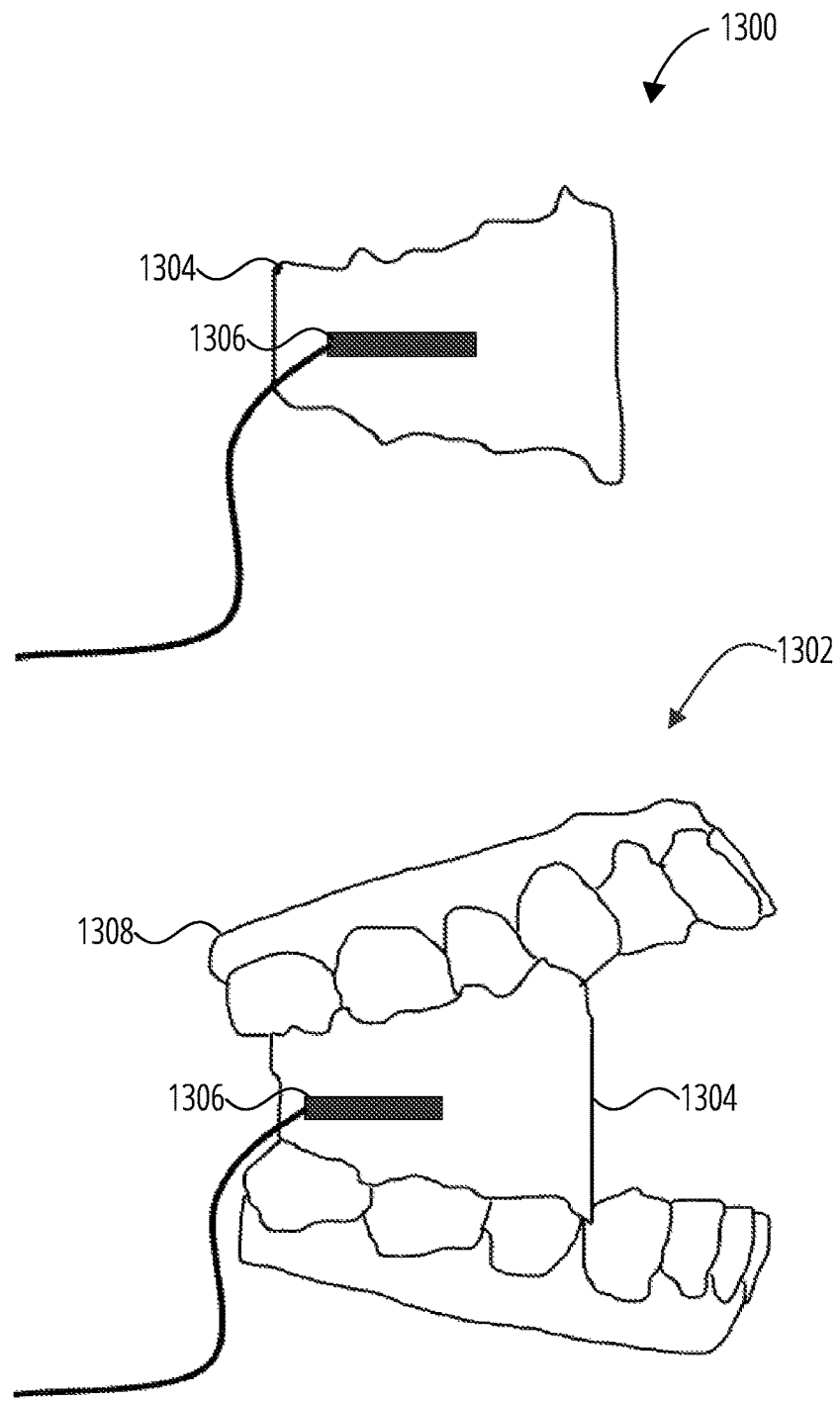
FIG. 13 illustrates a reference object in accordance with one example embodiment.

FIG. 13 illustrates a reference object in accordance with one example embodiment. The diagram 1300 illustrates a custom bite block 1304 that is customized to a bite of the patient 118 (e.g., the custom bite block 1304 is unique and based on the patient 118's bite). A micro sensor 1306 is coupled (e.g., embedded at a known position relative to the custom bite block 1304) to a predetermined location on the custom bite block 1304. The diagram 1302 illustrates the custom bite block 1304 temporarily coupled to the mouth 1308 of the patient 118. The patient 118 bites on the custom bite block 1304. As such, the location of a tooth in the mouth 1412 of the patient 118 can be determined relative to the custom bite block 1304 and the micro sensor 1306.

Figure 14:
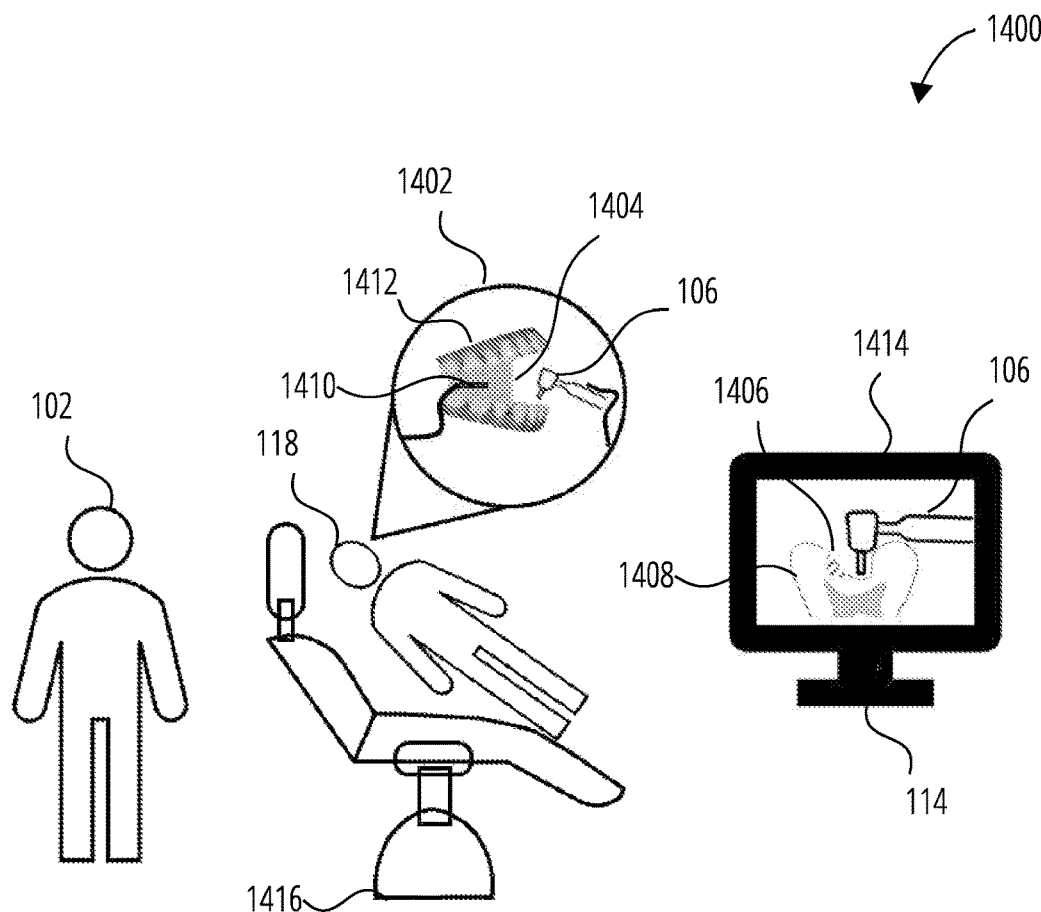
FIG. 14 illustrates an example operation of the reference object in accordance with one example embodiment.

FIG. 14 is a diagram 1400 illustrating an example operation of the custom bite block 1404 in accordance with one example embodiment. The enlargement 1402 illustrates the custom bite block 1404 coupled to the mouth 1412 of the patient 118. The patient 118 sits on a chair 1416.

The user 102 (e.g., a dentist) operates the dental device 106 in the mouth 1412 of the patient 118. The imaging system 114 includes a display 1414 that displays real-time (or near real-time) view of the location of the dental device 106 relative to a digital representation of a decay 1406 in the tooth 1408 of the patient 118. In other words, the display 1414 updates the information (e.g., image of the dental device 106 and augmented information representing the decay 1406) in real-time.

In another example embodiment, the presently described imaging system 114 can be used for other surgical operations where the user 102 operates on a portion of a body of the patient 118. For example, the imaging system 114 provides a visual indicator that points or highlights a portion of the real-time image of the portion of the body. Furthermore, the imaging system 114 provides guidance (via augmented reality information such as virtual arrows displayed on the real-time image) on how to operate on the portion of the body of the patient 118 based on the relative location of an instrument held by the user 102 and the portion of the body of the patient 118. The reference object 116 may be coupled to a predefined location on the portion of the body of the patient 118. As such, the distance and position of the instrument relative to the body of the patient 118 can be determined.

In one example embodiment, The MR guidance module 504 provides a visual guide to a user to visually guide a syringe to an injection site relative to a jawbone.

Figure 15:
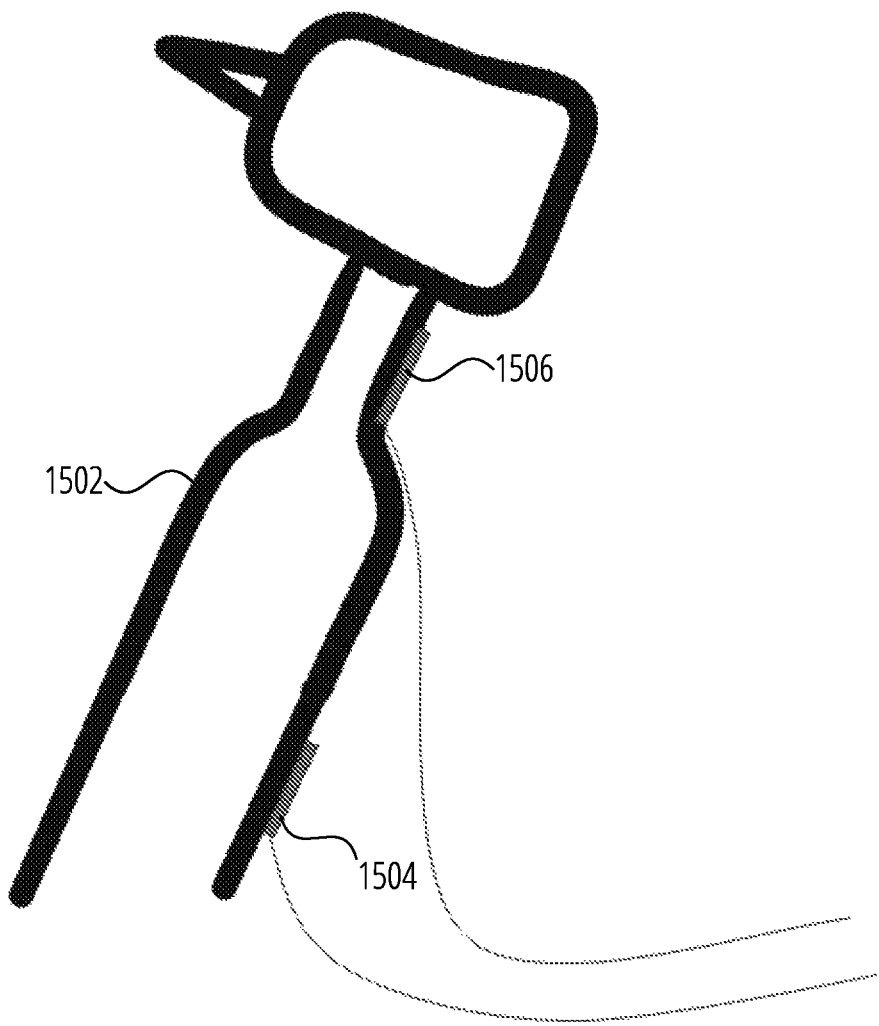
FIG. 15 illustrates an example of a dental instrument with inertial sensors in accordance with one example embodiment.

FIG. 15 illustrates an example of a dental device 106 with inertial sensors in accordance with one example embodiment. Examples of dental device 106 include a dental handpiece 1502, a scalpel, and a syringe. A sensor such as a micro tracker (e.g., sensor 1504, sensor 1506) is attached to the dental handpiece 1502. Exact geometries of the dental handpiece 1502 and attachments (e.g. dental burs) are known and digitized.

Figure 16:
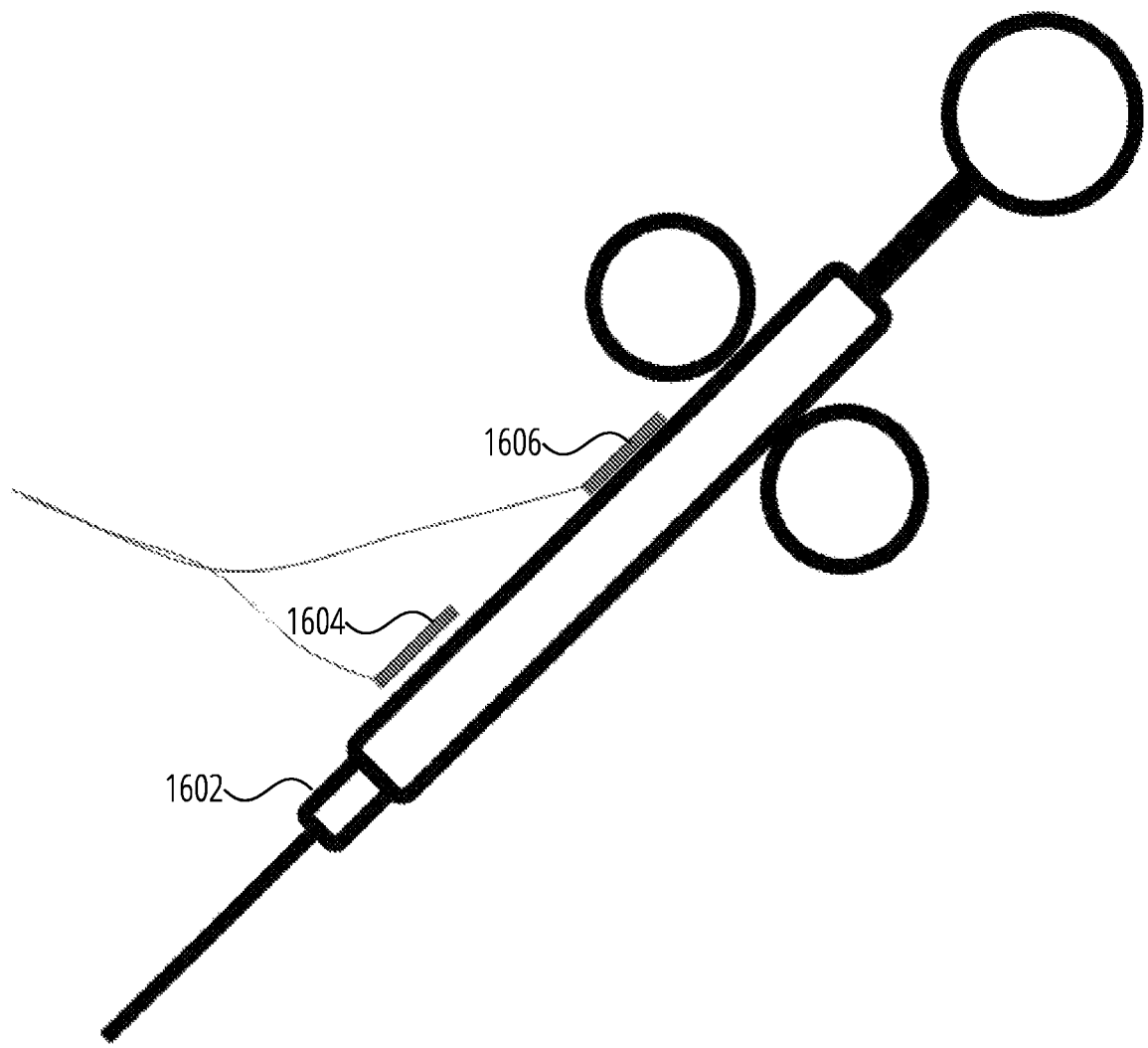
FIG. 16 illustrates a dental instrument with inertial sensors in accordance with one example embodiment.

FIG. 16 illustrates a dental instrument with inertial sensors in accordance with one example embodiment. Examples of dental device 106 include a syringe 1602. A sensor such as a microtracker (e.g., sensor 1604, sensor 1606) is attached to the dental handpiece 1502. Exact geometries of the dental handpiece 1502 and attachments (e.g. syringe needles) are known and digitized.

Figure 17:
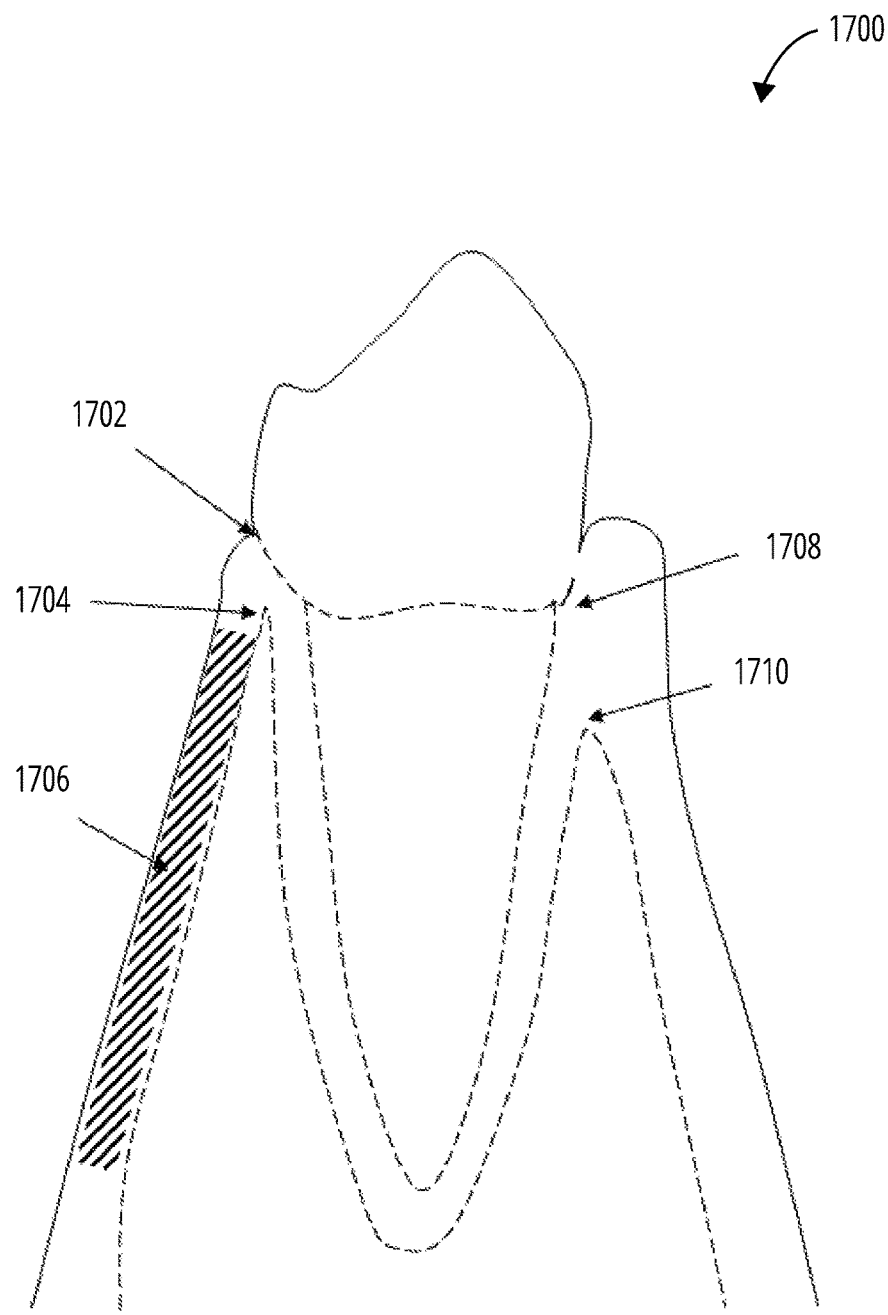
FIG. 17 illustrates a cross-section of a tooth in accordance with one example embodiment.

FIG. 17 illustrates a cross-section 1700 of a composite image of a tooth in accordance with one example embodiment. Examples of periodontal calculations performed by the composite image application 210 include:

Probing Depth (distance between top contact between tooth/gum and crest of bone—distance between point 1702 and point 1704)

Attachment Loss (periodontitis) (approximate height difference between enamel/root junction and alveolar bone crest—distance between point 1708 and point 1710)

Gingival Swelling (gingivitis) (probing depth+attachment loss−physiological pocket depth (about 2-3 mm))

Gingival biotype (thick or thin) (thickness depth between gum and supporting bone based average thickness of area 1706).

Figure 18:
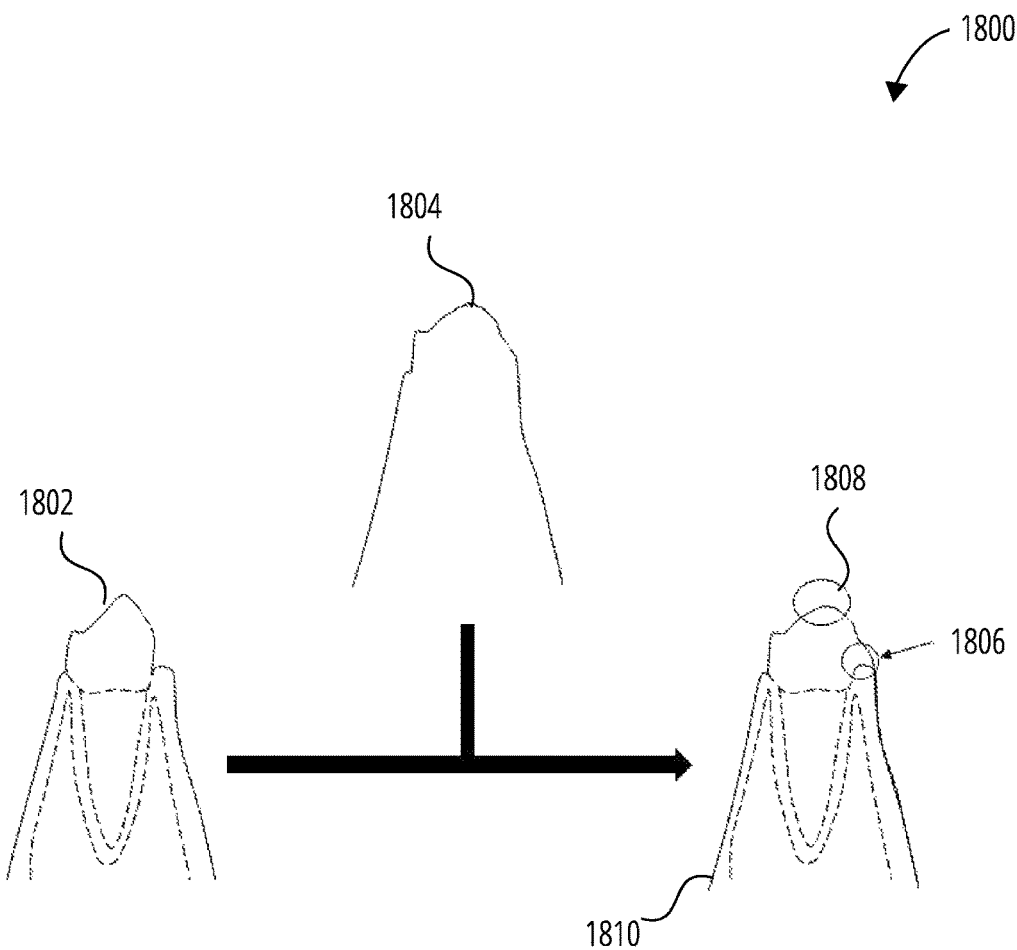
FIG. 18 illustrates a composite image of a cross-section of a tooth in accordance with one example embodiment.

FIG. 18 illustrates updating a composite image of a cross-section 1800 of a tooth in accordance with one example embodiment. The composite image 1802 can be updated based on additional data (e.g., updated geometric or colored data in a new scan of the same tooth). An updated image 1804 is combined to the composite image 1802 to generate an updated composite image 1810.

Differences from the composite image 1802 and the updated image 1804 are indicated in the updated composite image 1810. For example, the differences include an area of surface addition 1806 and an area of surface wear 1808. The area of surface addition 1806 and area of surface wear 1808 can be used to identify areas of tartar buildup and gingivitis.

Figure 19:
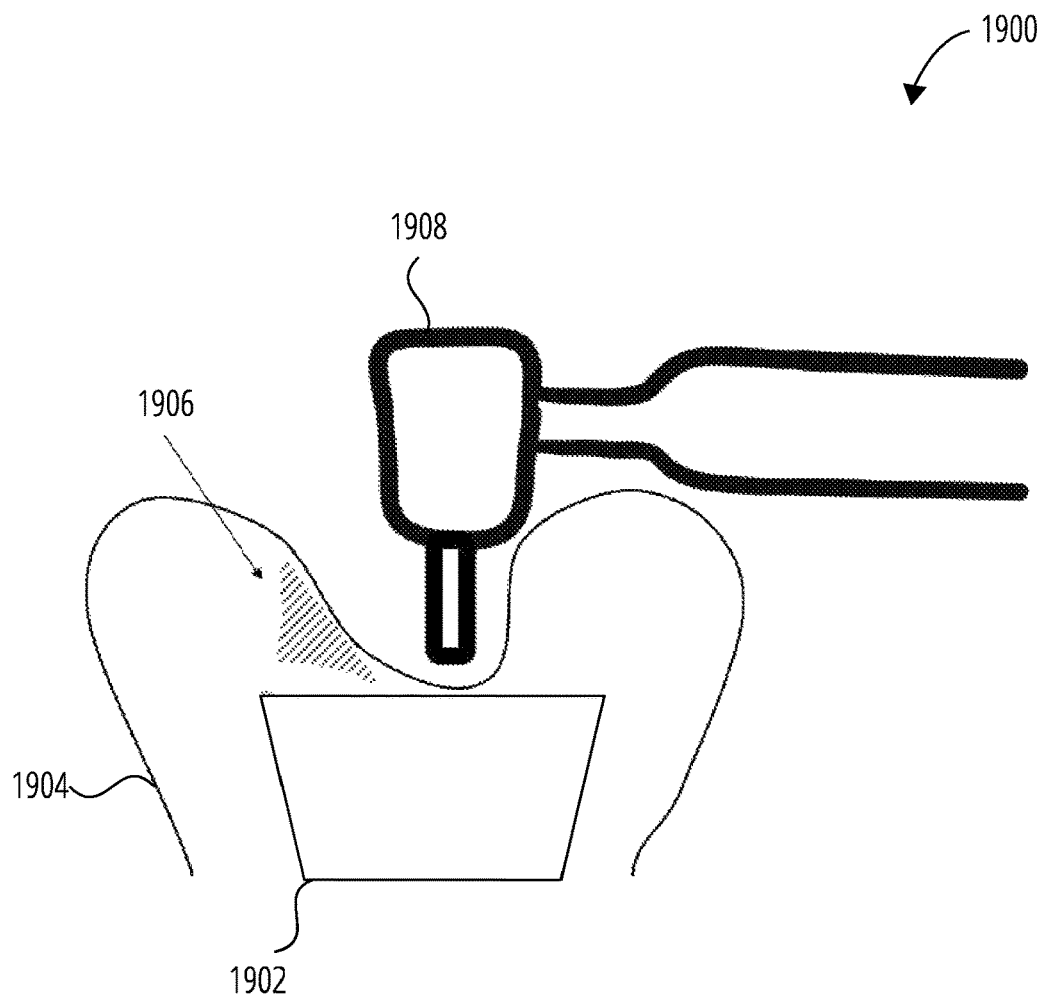
FIG. 19 illustrates an example operation of the imaging system in accordance with one example embodiment.

FIG. 19 illustrates an example operation 1900 of the imaging system in accordance with one example embodiment. The tooth surface 1904 and tooth nerve 1902 are displayed in the display 204. The display 204 also displays the decay area 1906 on the corresponding area on the tooth surface 1904. The MR guidance module 504 provides a visual guide for the dental instrument 1908 of the user 102 to the decay area 1906.

Figure 20:
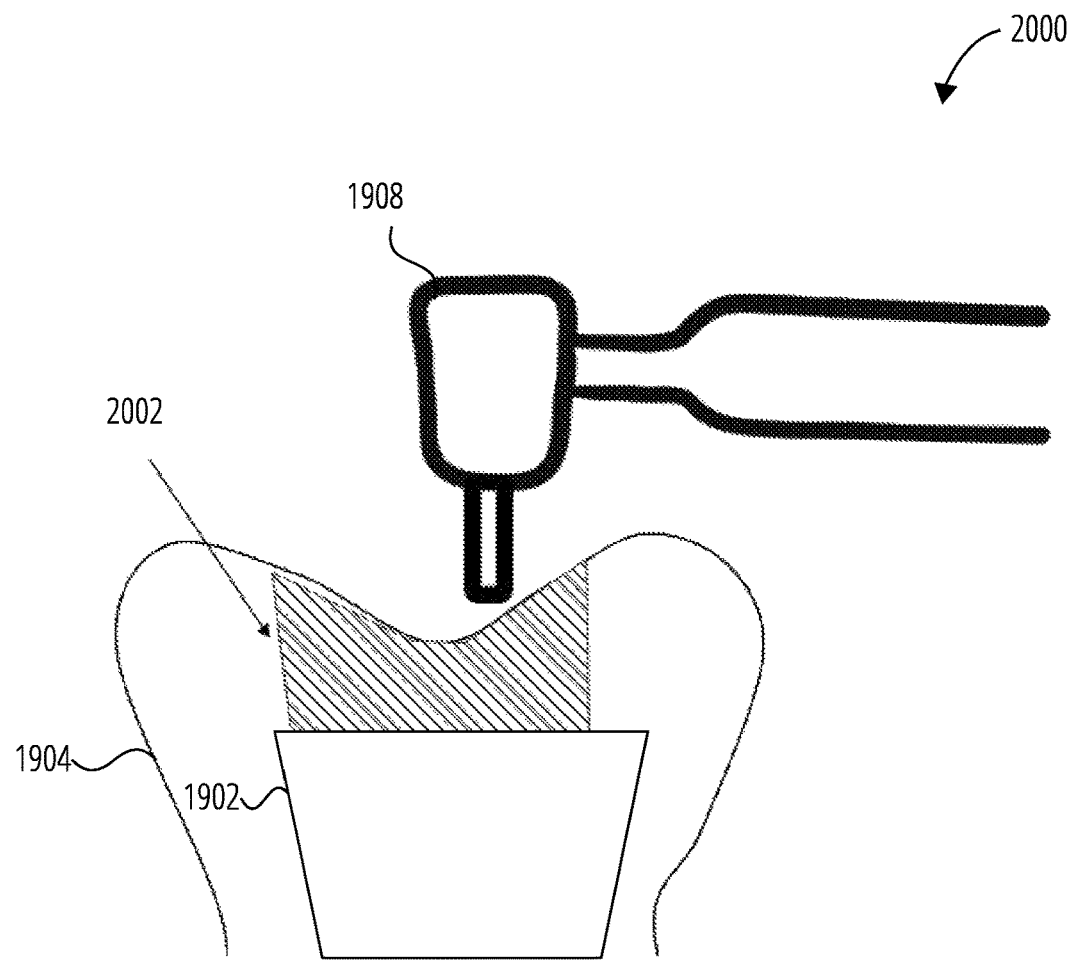
FIG. 20 illustrates another example operation of the imaging system in accordance with one example embodiment.

FIG. 20 illustrates another example operation 2000 of the imaging system in accordance with one example embodiment. The tooth surface 1904 and tooth nerve 1902 are displayed in the display 204. The MR guidance module 504 provides a visual guide for the dental instrument 1908 to the root canal shape 2002.

Figure 21:
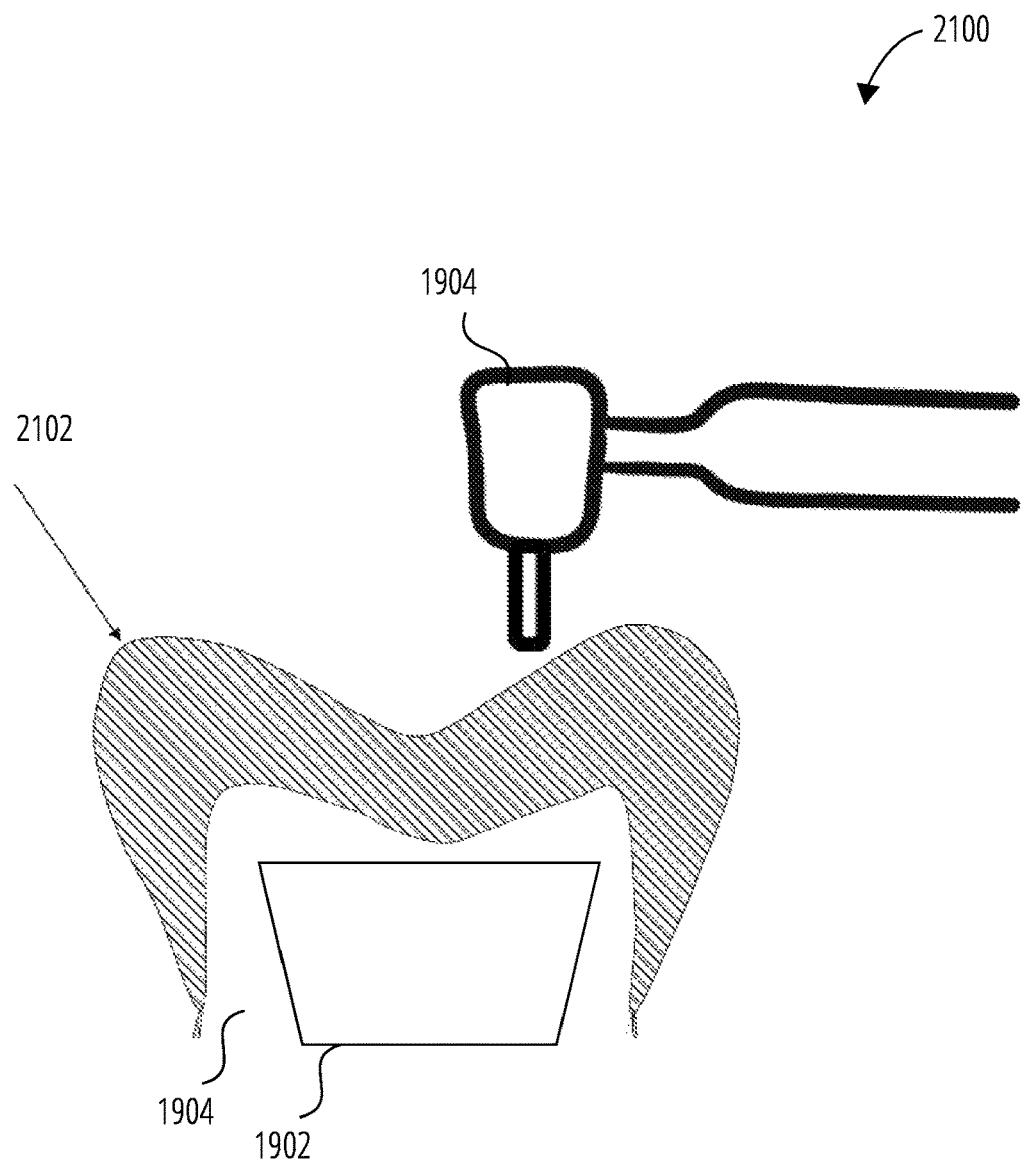
FIG. 21 illustrates another example operation of the imaging system in accordance with one example embodiment.

FIG. 21 illustrates another example operation 2100 of the imaging system in accordance with one example embodiment. The MR guidance module 504 provides a visual guide for the dental instrument 1908 to bur the tooth shape to be removed 2102.

Figure 22:
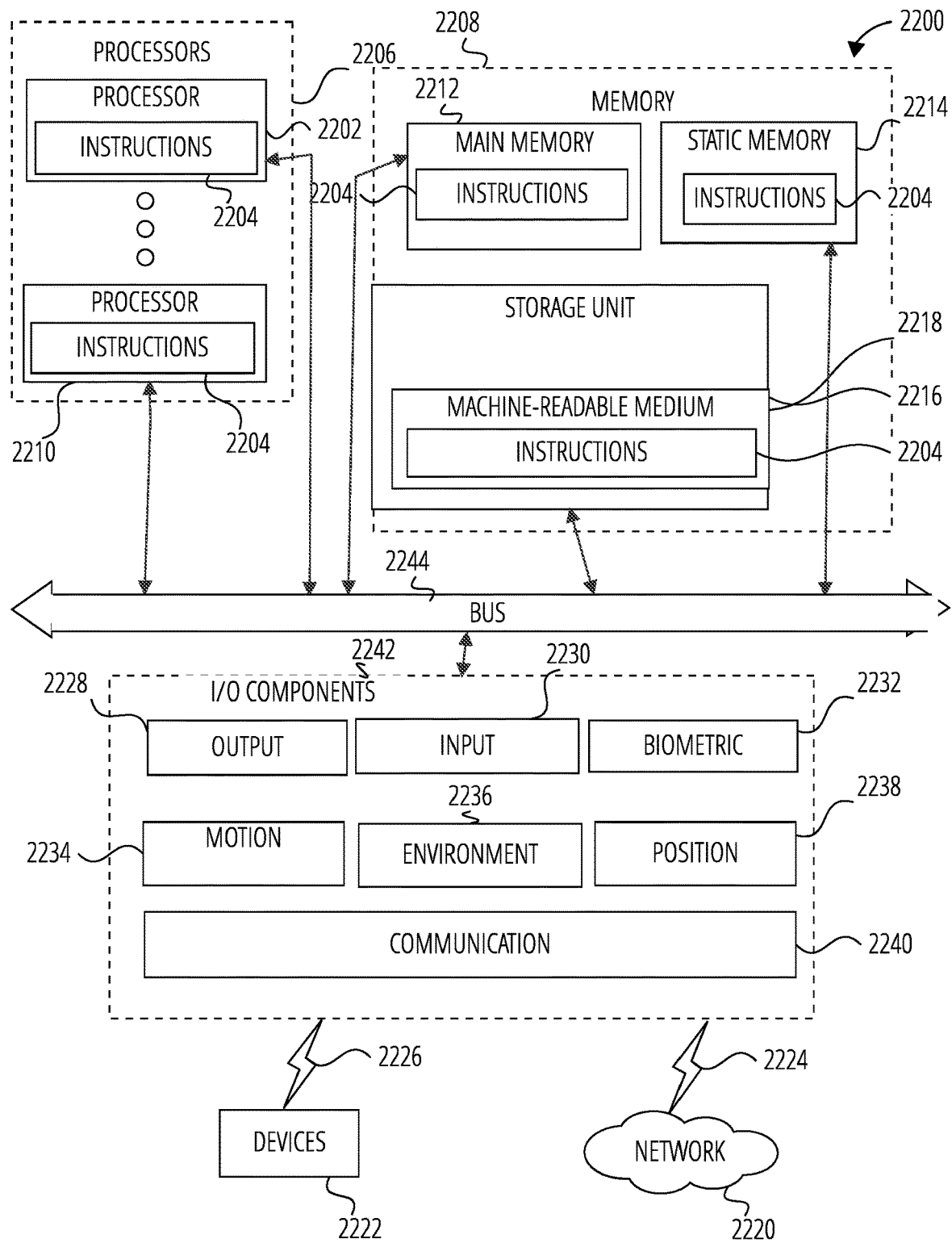
FIG. 22 is a diagrammatic representation of a machine in the form of a computer system within which a set of instructions may be executed for causing the machine to perform any one or more of the methodologies discussed herein, according to an example embodiment.

FIG. 22 is a diagrammatic representation of the machine 2200 within which instructions 2204 (e.g., software, a program, an application, an applet, an app, or other executable code) for causing the machine 2200 to perform any one or more of the methodologies discussed herein may be executed. For example, the instructions 2204 may cause the machine 2200 to execute any one or more of the methods described herein. The instructions 2204 transform the general, non-programmed machine 2200 into a particular machine 2200 programmed to carry out the described and illustrated functions in the manner described. The machine 2200 may operate as a standalone device or may be coupled (e.g., networked) to other machines. In a networked deployment, the machine 2200 may operate in the capacity of a server machine or a client machine in a server-client network environment, or as a peer machine in a peer-to-peer (or distributed) network environment. The machine 2200 may comprise, but not be limited to, a server computer, a client computer, a personal computer (PC), a tablet computer, a laptop computer, a netbook, a set-top box (STB), a PDA, an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 2204, sequentially or otherwise, that specify actions to be taken by the machine 2200. Further, while only a single machine 2200 is illustrated, the term "machine" shall also be taken to include a collection of machines that individually or jointly execute the instructions 2204 to perform any one or more of the methodologies discussed herein.

The machine 2200 may include processors 2206, memory 2208, and I/O components 2242, which may be configured to communicate with each other via a bus 2244. In an example embodiment, the processors 2206 (e.g., a Central Processing Unit (CPU), a Reduced Instruction Set Computing (RISC) Processor, a Complex Instruction Set Computing (CISC) Processor, a Graphics Processing Unit (GPU), a Digital Signal Processor (DSP), an ASIC, a Radio-Frequency Integrated Circuit (RFIC), another Processor, or any suitable combination thereof) may include, for example, a Processor 2202 and a Processor 2210 that execute the instructions 2204. The term "Processor" is intended to include multi-core processors that may comprise two or more independent processors (sometimes referred to as "cores") that may execute instructions contemporaneously. Although FIG. 22 shows multiple processors 2206, the machine 2200 may include a single Processor with a single core, a single Processor with multiple cores (e.g., a multi-core Processor), multiple processors with a single core, multiple processors with multiples cores, or any combination thereof.

The memory 2208 includes a main memory 2212, a static memory 2214, and a storage unit 2216, both accessible to the processors 2206 via the bus 2244. The main memory 2208, the static memory 2214, and storage unit 2216 store the instructions 2204 embodying any one or more of the methodologies or functions described herein. The instructions 2204 may also reside, completely or partially, within the main memory 2212, within the static memory 2214, within machine-readable medium 2218 within the storage unit 2216, within at least one of the processors 2206 (e.g., within the Processor's cache memory), or any suitable combination thereof, during execution thereof by the machine 2200.

The I/O components 2242 may include a wide variety of components to receive input, provide output, produce output, transmit information, exchange information, capture measurements, and so on. The specific I/O components 2242 that are included in a particular machine will depend on the type of machine. For example, portable machines such as mobile phones may include a touch input device or other such input mechanisms, while a headless server machine will likely not include such a touch input device. It will be appreciated that the I/O components 2242 may include many other components that are not shown in FIG. 22. In various example embodiments, the I/O components 2242 may include output components 2228 and input components 2230. The output components 2228 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 2230 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), and the like.

In further example embodiments, the I/O components 2242 may include biometric components 2232, motion components 2234, environmental components 2236, or position components 2238, among a wide array of other components. For example, the biometric components 2232 include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 2234 include acceleration sensor components (e.g., accelerometer), gravitation sensor components, rotation sensor components (e.g., gyroscope), and so forth. The environmental components 2236 include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 2238 include location sensor components (e.g., a GPS receiver Component), altitude sensor components (e.g., altimeters or barometers that detect air pressure from which altitude may be derived), orientation sensor components (e.g., magnetometers), and the like.

Communication may be implemented using a wide variety of technologies. The I/O components 2242 further include communication components 2240 operable to couple the machine 2200 to a network 2220 or devices 2222 via a coupling 2224 and a coupling 2226, respectively. For example, the communication components 2240 may include a network interface Component or another suitable device to interface with the network 2220. In further examples, the communication components 2240 may include wired communication components, wireless communication components, cellular communication components, Near Field Communication (NFC) components, Bluetooth® components (e.g., Bluetooth® Low Energy), WiFi® components, and other communication components to provide communication via other modalities. The devices 2222 may be another machine or any of a wide variety of peripheral devices (e.g., a peripheral device coupled via a USB).

Moreover, the communication components 2240 may detect identifiers or include components operable to detect identifiers. For example, the communication components 2240 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 2240, such as location via Internet Protocol (IP) geolocation, location via Wi-Fi® signal triangulation, location via detecting an NFC beacon signal that may indicate a particular location, and so forth.

The various memories (e.g., memory 2208, main memory 2212, static memory 2214, and/or memory of the processors 2206) and/or storage unit 2216 may store one or more sets of instructions and data structures (e.g., software) embodying or used by any one or more of the methodologies or functions described herein. These instructions (e.g., the instructions 2204), when executed by processors 2206, cause various operations to implement the disclosed embodiments.

The instructions 2204 may be transmitted or received over the network 2220, using a transmission medium, via a network interface device (e.g., a network interface Component included in the communication components 2240) and using any one of a number of well-known transfer protocols (e.g., hypertext transfer protocol (HTTP)). Similarly, the instructions 2204 may be transmitted or received using a transmission medium via the coupling 2226 (e.g., a peer-to-peer coupling) to the devices 2222.

Although an embodiment has been described with reference to specific example embodiments, it will be evident that various modifications and changes may be made to these embodiments without departing from the broader scope of the present disclosure. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

EXAMPLES

Example 1 includes a method comprising: accessing first imaging data of a specimen using a first sensor device, the first imaging data comprising volumetric data; accessing second imaging data of the specimen using a second sensor device, the second imaging data comprising surface data; registering a common anatomical region of the specimen in the first imaging data and the second imaging data; and generating a composite image based on the registered common anatomical region, the composite image indicating the volumetric data and the surface data of the specimen.

Example 2 includes example 1, further comprising: determining clinical measurements of the specimen based on the first and second imaging data; generating a three-dimensional model of the specimen based on the clinical measurements and the composite image; and measuring dental periodontal health with the three-dimensional model of the specimen.

Example 3 includes any of the above examples, wherein the clinical measurements indicate at least one of a pocket depth, a tissue biotype, areas of inflammation and tissue damage, exposure of dental furcation, or dental attachment loss.

Example 4 includes any of the above examples, wherein registering the common anatomical region further comprises: identifying the common anatomical region of the specimen in the first imaging data and the second imaging data; and aligning the first imaging data with the second imaging data based on the identified common anatomical region.

Example 5 includes any of the above examples, wherein the first sensor tool comprises a cone beam CT scan, the first imaging data indicating bone volume of the specimen, wherein the second sensor tool comprises an intraoral scan, the volumetric data comprising coloring attributes corresponding to tissue quality of the specimen.

Example 6 includes any of the above examples, further comprising: accessing first sensor data of a reference object resting in a mouth of a patient, the reference object being at a predefined position relative to the mouth of the patient; accessing second sensor data of a sensor coupled to a dental instrument; determining a position of the dental instrument relative to the reference object based on the first and second sensor data; and displaying a virtual representation of the dental instrument relative to a virtual representation of the mouth of the patient based on the position of the dental instrument relative to the reference object.

Example 7 includes any of the above examples, further comprising: providing a patient with a bite block that has been customized to fit the patient, the bite block configured to be temporarily locked with the upper and lower jaw of the patient, the bite block forming a predefined frame of reference based on the position of the bite block relative to a tooth of the patient; accessing position data from a position sensor attached to a dental instrument, the position data being relative to the bite block; computing a relative position between the dental instrument and a region of interest of the patient; and displaying, a virtual position of the dental instrument relative to a 3D model of a mouth of the patient in real time, based on the relative position between the dental instrument and the region of interest, wherein the 3D model is based on the composite image.

Example 8 includes any of the above examples, further comprising: indicating a tooth decay area and a dental nerve area in a display of the 3D model.

Example 9 includes any of the above examples, further comprising: indicating a suggested shape for a root canal in a display of the 3D model.

Example 10 includes any of the above examples, further comprising: indicating a dental nerve area and a tooth removal area for a crown procedure in a display of the 3D model.

Example 11 includes any of the above examples, further comprising: indicating a bone region of a projected injection site in a display of the 3D model.

Example 12 includes any of the above examples, wherein the second imaging data is based on at least one of a fluorescent image with excitation wavelength of about 270 nm to about 370 nm, emission wavelength of about 305 nm to about 500 nm, near-infrared imaging that indicates reflectance and transmission, or optical coherence tomography in the near infrared spectrum.

Example 13 includes any of the above examples, further comprising: accessing updated imaging data of the specimen using the first or second sensor device; updating the composite image based on the third imaging data; and identifying a region of difference based on the updated composite image and the composite image, the region of difference indicating an area of surface wear on a tooth or an area of surface addition on the tooth.

Example 14 includes any of the above examples, further comprising: identifying a region of interest in the composite image based on an analysis of the first or second imaging data; generating a virtual indicator that indicates the region of interest; causing a display of the virtual indicator in the composite image or an image of the specimen; and operating the dental instrument with a robotic device that is configured to operate on the specimen at the region of interest.

Example 15 includes a computing apparatus, the computing apparatus comprising: a Processor; and a memory storing instructions that, when executed by the Processor, configure the apparatus to: access first imaging data of a specimen using a first sensor device, the first imaging data comprising volumetric data; access second imaging data of the specimen using a second sensor device, the second imaging data comprising surface data; and generate a composite image based on the first and second imaging data, the composite image indicating the volumetric data and the surface data of the specimen.

What is claimed is:

1. A method comprising:
accessing first imaging data of a specimen using a first sensor device, the first imaging data comprising volumetric data;
accessing second imaging data of the specimen using a second sensor device, the second imaging data comprising surface data;
registering a common anatomical region of the specimen in the first imaging data and the second imaging data;
generating a composite image based on the registered common anatomical region, the composite image indicating the volumetric data and the surface data of the specimen, wherein the first sensor tool comprises a cone beam CT scan, the first imaging data indicating bone volume of the specimen, wherein the second sensor tool comprises an intraoral scan;
accessing first sensor data of a reference object resting in a mouth of a patient, the reference object being at a predefined position relative to the mouth of the patient;
accessing second sensor data of a sensor coupled to a dental instrument;
determining a position of the dental instrument relative to the reference object based on the first and second sensor data; and
displaying a virtual representation of the dental instrument relative to a virtual representation of the mouth of the patient based on the position of the dental instrument relative to the reference object.

2. The method of claim 1, further comprising:
determining clinical measurements of the specimen based on the first and second imaging data;
generating a three-dimensional model of the specimen based on the clinical measurements and the composite image; and
measuring dental periodontal health with the three-dimensional model of the specimen.

3. The method of claim 2, wherein the clinical measurements indicate at least one of a pocket depth, a tissue biotype, areas of inflammation and tissue damage, exposure of dental furcation, or dental attachment loss.

4. The method of claim 1, wherein registering the common anatomical region further comprises:
identifying the common anatomical region of the specimen in the first imaging data and the second imaging data; and
aligning the first imaging data with the second imaging data based on the identified common anatomical region.

5. The method of claim 1, wherein the volumetric data comprising coloring attributes corresponding to tissue quality of the specimen.

6. The method of claim 1,
wherein the reference object comprises a bite block that has been customized to fit the mouth of the patient, the bite block configured to be temporarily locked with the upper and lower jaw of the patient, the bite block forming a predefined frame of reference based on the position of the bite block relative to a tooth of the patient; and
wherein the method further comprises:
accessing position data from a position sensor attached to the dental instrument, the position data being relative to the bite block;
computing a relative position between the dental instrument and a region of interest of the patient; and
displaying, a virtual position of the dental instrument relative to a 3D model of the mouth of the patient in real time, based on the relative position between the dental instrument and the region of interest, wherein the 3D model is based on the composite image.

7. The method of claim 6, further comprising:
indicating a tooth decay area and a dental nerve area in a display of the 3D model.

8. The method of claim 6, further comprising:
indicating a suggested shape for a root canal in a display of the 3D model.

9. The method of claim 6, further comprising:
indicating a dental nerve area and a tooth removal area for a crown procedure in a display of the 3D model.

10. The method of claim 6, further comprising:
indicating a bone region of a projected injection site in a display of the 3D model.

11. The method of claim 1, wherein the second imaging data is based on at least one of a fluorescent image with excitation wavelength of about 270 nm to about 370 nm, emission wavelength of about 305 nm to about 500 nm, near-infrared imaging that indicates reflectance and transmission, or optical coherence tomography in the near infrared spectrum.

12. The method of claim 1, further comprising:
accessing updated imaging data of the specimen using the first or second sensor device;
updating the composite image based on the third imaging data; and
identifying a region of difference based on the updated composite image and the composite image, the region of difference indicating an area of surface wear on a tooth or an area of surface addition on the tooth.

13. The method of claim 1, further comprising:
identifying a region of interest in the composite image based on an analysis of the first or second imaging data;
generating a virtual indicator that indicates the region of interest;
causing a display of the virtual indicator in the composite image or an image of the specimen; and
operating the dental instrument with a robotic device that is configured to operate on the specimen at the region of interest.

14. A computing apparatus, the computing apparatus comprising:
a processor; and
a memory storing instructions that, when executed by the processor, configure the apparatus to perform operations comprising:
access first imaging data of a specimen using a first sensor device, the first imaging data comprising volumetric data;
access second imaging data of the specimen using a second sensor device, the second imaging data comprising surface data;
register a common anatomical region of the specimen in the first imaging data and the second imaging data;
generate a composite image based on the registered common anatomical region, the composite image indicating the volumetric data and the surface data of the specimen, wherein the first sensor tool comprises a cone beam CT scan, the first imaging data indicating bone volume of the specimen, wherein the second sensor tool comprises an intraoral scan;
access first sensor data of a reference object resting in a mouth of a patient, the reference object being at a predefined position relative to the mouth of the patient;
access second sensor data of a sensor coupled to a dental instrument;
determine a position of the dental instrument relative to the reference object based on the first and second sensor data; and
display a virtual representation of the dental instrument relative to a virtual representation of the mouth of the patient based on the position of the dental instrument relative to the reference object.

15. The computing apparatus of claim 14, wherein the instructions further configure the apparatus to:
determine clinical measurements of the specimen based on the first and second imaging data;
generate a three-dimensional model of the specimen based on the clinical measurements and the composite image; and
measure dental periodontal health with the three-dimensional model of the specimen.

16. The computing apparatus of claim 15, wherein the clinical measurements indicate at least one of a pocket depth, a tissue biotype, areas of inflammation and tissue damage, exposure of dental furcation, or dental attachment loss,
wherein the volumetric data comprising coloring attributes corresponding to tissue quality of the specimen.

17. The computing apparatus of claim 14,
wherein the reference object comprises a bite block that has been customized to fit the mouth of the patient, the bite block configured to be temporarily locked with the upper and lower jaw of the patient, the bite block forming a predefined frame of reference based on the position of the bite block relative to a tooth of the patient; and
wherein the instructions further configure the apparatus to:
access position data from a position sensor attached to a dental instrument, the position data being relative to the bite block;
compute a relative position between the dental instrument and a region of interest of the patient; and display, a virtual position of the dental instrument relative to a 3D model of the mouth of the patient in real time, based on the relative position between the dental instrument and the region of interest, wherein the 3D model is based on the composite image.

18. A non-transitory computer-readable storage medium, the computer-readable storage medium including instructions that when executed by a computer, cause the computer to perform operations comprising:
   access first imaging data of a specimen using a first sensor device, the first imaging data comprising volumetric data;
   access second imaging data of the specimen using a second sensor device, the second imaging data comprising surface data;
   register a common anatomical region of the specimen in the first imaging data and the second imaging data;
   generate a composite image based on the registered common anatomical region, the composite image indicating the volumetric data and the surface data of the specimen, wherein the first sensor tool comprises a cone beam CT scan, the first imaging data indicating bone volume of the specimen, wherein the second sensor tool comprises an intraoral scan;
   access first sensor data of a reference object resting in a mouth of a patient, the reference object being at a predefined position relative to the mouth of the patient;
   access second sensor data of a sensor coupled to a dental instrument;
   determine a position of the dental instrument relative to the reference object based on the first and second sensor data; and
   display a virtual representation of the dental instrument relative to a virtual representation of the mouth of the patient based on the position of the dental instrument relative to the reference object.

\* \* \* \* \*